United States Patent
Chin et al.

(10) Patent No.: US 8,158,631 B2
(45) Date of Patent: Apr. 17, 2012

(54) HETEROCYCLIC ANTIVIRAL COMPOUNDS

(75) Inventors: Elbert Chin, San Jose, CA (US); Javier de Vicente Fidalgo, Glen Ridge, NJ (US); Jim Li, San Francisco, CA (US); Alfred Sui-Ting Lui, Sunnyvale, CA (US); Kristen Lynn McCaleb, Daly City, CA (US); Ryan Craig Schoenfeld, San Jose, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 0 days.

(21) Appl. No.: 12/822,630

(22) Filed: Jun. 24, 2010

(65) Prior Publication Data

US 2010/0330032 A1 Dec. 30, 2010

Related U.S. Application Data

(60) Provisional application No. 61/219,977, filed on Jun. 24, 2009.

(51) Int. Cl.
*A61K 31/497* (2006.01)
*C07D 241/02* (2006.01)

(52) U.S. Cl. ...................... 514/252.1; 544/224; 544/242; 544/336

(58) Field of Classification Search .................. 544/224, 544/242, 336; 514/247, 252.1
See application file for complete search history.

(56) References Cited

FOREIGN PATENT DOCUMENTS

| WO | WO00/09543 A2 | 2/2000 |
|---|---|---|
| WO | WO01/85172 A1 | 11/2001 |
| WO | 2009032116 A1 | 3/2009 |
| WO | 2009032123 A2 | 3/2009 |
| WO | 2009032125 A1 | 3/2009 |
| WO | 2009039127 A1 | 3/2009 |
| WO | 2009039134 A1 | 3/2009 |
| WO | WO2009/039135 A1 | 3/2009 |
| WO | 2009064848 A1 | 5/2009 |
| WO | 2009064852 A1 | 5/2009 |
| WO | WO2010/111436 A2 | 9/2010 |
| WO | WO2010/111437 A1 | 9/2010 |

*Primary Examiner* — Paul V. Ward
(74) *Attorney, Agent, or Firm* — Brian L. Buckwalter

(57) ABSTRACT

Compounds having the formula I wherein $R^1$, $R^2$, $R^3$, $R^4$, and $R^5$ are as defined herein are Hepatitis C virus NS5b polymerase inhibitors. Also disclosed are compositions and methods for treating an HCV infection and inhibiting HCV replication.

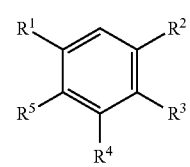

(I)

15 Claims, No Drawings

HETEROCYCLIC ANTIVIRAL COMPOUNDS

CROSS REFERENCE TO PRIOR APPLICATIONS

This application claims the benefit of priority to U.S. Ser. No. 61/219,977 filed Jun. 24, 2009 which is hereby incorporated by reference in it entirety.

FIELD OF THE INVENTION

The present invention provides non-nucleoside compounds of formula I, and certain derivatives thereof, which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae*: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forms and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investig. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Boceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

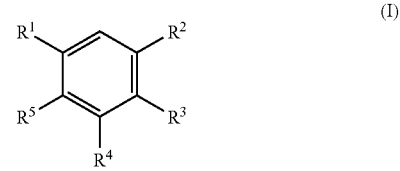

(I)

The present invention provides a compound according to formula I, or a pharmaceutically acceptable salt thereof wherein $R^1$, $R^2$, $R^3$, $R^4$, $R^5$ are as follows:

$R^1$ is a (i) heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, 1,1-dioxo-dioxo-1$\lambda^6$-isothiazolidin-2-yl and 1,1-dioxo-1$\lambda^6$-[1,2,6]thiadiazinan-2-yl, said heterocycle optionally substituted with one or two substitutents independently selected from $C_{1-6}$ alkyl or halogen, or, (ii) a heteroaryl moiety selected from the group consisting of 2-oxo-2(H)-pyridin-1-yl, 6-oxo-6H-pyridazin-1-yl, 6-oxo-6H-pyrimidin-1-yl, 2-oxo-2H-pyrazin-1-yl and 5-oxo-1,5-dihydro-[1,2,4]triazol-4-yl said heteroaryl moiety optionally independently substituted with one or two halogen or $C_{1-3}$ alkyl substitutents.

$R^2$ is (a) —$CR^{2a}$=$CR^{2a}$Ar, (b) —$(C(R^{2b})_2)_n$Ar, (c) —X[C($R^6)_2]_p$NR$^a$R$^b$ wherein X is O or NR$^7$, $R^7$ is hydrogen or $C_{1-4}$ alkyl, $R^6$ is independently in each occurrence hydrogen, $C_{1-3}$ alkyl or two $R^6$ residues on the same carbon are $C_{2-5}$ alkylene or two $R^6$ residues on different carbons are $C_{1-4}$ alkylene, (d) 1-oxo-1H-isochromen-7-yl or 2H-isoquinolin-1-one either optionally substituted by NR$^a$R$^b$, or, (e) benzooxazol-2-yl or benzothiazol-2-yl either optionally substituted by NR$^a$R$^b$.

$R^{2a}$ is independently in each occurrence hydrogen, $C_{1-3}$ alkyl, cyano, carboxyl or halogen.

$R^{2b}$ is independently in each occurrence hydrogen or $C_{1-3}$ alkyl, cyano, carboxyl, $C_{1-3}$ hydroxyalkyl or $C_{1-3}$ alkoxy-$C_{1-3}$ alkyl.

$R^3$ is hydrogen, $C_{1-6}$ alkoxy, $C_{1-6}$ alkyl, $C_{1-6}$ haloalkyl, $C_{1-6}$ haloalkoxy or halogen or $R^3$ and $R^{4a}$ together are CH$_2$—O or (CH$_2$)$_2$ and together with atoms to which they are attached form a 2,3-dihydrobenzofuran or an indane.

Ar is (a) aryl or naphthyl, or (b) heteroaryl wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, $C_{1-3}$ alkoxy-$C_{1-6}$ alkyl, halogen, (CH$_2$)$_n$NR$^a$R$^b$, cyano, $C_{1-6}$ alkoxycarbonyl, carbamoyl, N-alkylcarbamoyl, N,N-dialkylcarbamoyl, (CH$_2$)$_n$CO$_2$H, SO$_2$NH$_2$, $C_{1-6}$ alkylsulfinyl and $C_{1-6}$ alkylsulfonyl.

$R^a$ and $R^b$ are independently hydrogen, $C_{1-6}$ alkyl, $C_{1-6}$ haloalkyl, $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, —SO$_2$—NR$^c$R$^d$, $C_{1-3}$ alkylcarbamoyl or $C_{1-3}$ dialkylcarbamoyl.

$R^c$ and $R^d$ are (i) independently hydrogen, $C_{1-3}$ alkyl or (CH$_2$)$_{2-6}$NR$^e$R$^f$ or (ii) together with the nitrogen to which they are attached are $(CH_2)_2X^5(CH_2)_2$ wherein $X^5$ is O or $NR^i$ and $R^i$ is hydrogen, $C_{1-3}$ alkyl, $C_{1-3}$ acyl or $C_{1-3}$ alkylsulfonyl.

$R^e$ and $R^f$ are independently in each occurrence hydrogen or $C_{1-3}$ alkyl.

$R^4$ is hydrogen, $C_{1-6}$ alkyl, $C_{1-6}$ haloalkyl, $C_{3-5}$ cycloalkyl, halogen, $C_{1-6}$ alkoxy, $C_{1-3}$ halo alkoxy or $CR^{4a}R^{4b}R^{4c}$ wherein: (i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxy; or (ii) when taken together, $R^{4a}$ and $R^{4b}$ together are $C_{2-4}$ alkylene and $R^{4b}$ is hydrogen, $C_{1-3}$ alkyl, $C_{1-2}$ alkoxy, halogen, $C_{1-3}$ hydroxyalkyl, cyano or $C_{1-2}$ fluoroalkyl, or $R^{4a}$ and Rob together with the carbon to which they are attached are 3-oxetanyl, or tetrahydrofuran-2-yl; or, (iii) either $R^5$ or $R^3$ and $R^{4a}$ together are $CH_2$—O or $(CH_2)_2$ and together with atoms to which they are attached form a 2,3-dihydro-benzofuran or an indane and $R^{4b}$ and $R^{4c}$ are $C_{1-3}$ alkyl.

$R^5$ is hydrogen or halogen or $R^5$ and $R^{4a}$ together are $CH_2$—O or $(CH_2)_2$ and together with atoms to which they are attached form a 2,3-dihydrobenzofuran or an indane.

n is independently in each occurrence zero to three; or;

a pharmaceutically acceptable salt thereof.

Compounds of general formula I can be either neutral compounds or a pharmaceutically acceptable salt thereof.

The present invention also provides a method for treating a disease a Hepatitis C Virus (HCV) virus infection by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ----- "drawn through a bond each refer to the point of attachment of a functional group or other chemical moiety to the rest of the molecule of which it is a part. Thus, for example:

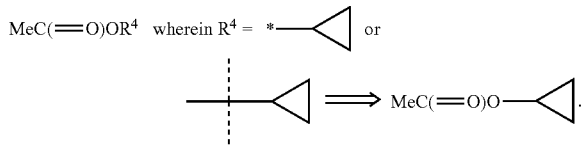

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, α-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain a basic center and suitable acid addition salts are formed from acids which form non-toxic salts. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to formula I wherein $R^1$, $R^2$, $R^3$, $R^4$ and $R^5$ are as described here above. In all other embodiments provided below, substituents which can be present in each embodiment and which are not explicitly defined retain the broadest definition provided in the Summary of the Invention.

In another embodiment of the present invention I wherein $R^1$ is a (i) heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, 1,1-dioxo-1$\lambda^6$ isothiazolidin-2-yl and 1,1-dioxo-1$\lambda^6$-[1,2,6] thiadiazinan-2-yl said heterocycle optionally substituted with one or two substitutents independently selected from $C_{1-6}$ alkyl, or (ii) a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl said heteroaryl moiety optionally independently substituted with one or two halogen substitutents; $R^2$ is (a) —$CR^{2a}$=$CR^{2a}$Ar, (b) —$(C(R^{2b})_2)_n$Ar (c) 1-oxo-isochromen-3-yl optionally substituted by $NR^aR^b$ or (d) benzooxazol-2-yl optionally substituted by $NR^aR^b$; $R^{2a}$ and $R^{2b}$ in each occurrence are hydrogen; $R^3$ is hydrogen or $C_{1-6}$ alkoxy; Ar is phenyl wherein said phenyl is optionally independently substituted with one to three substitutents selected from the group consisting of $C_{1-6}$ hydroxyalkyl, $C_{1-3}$ alkoxy-$C_{1-6}$ alkyl, $(CH_2)_nNR^aR^b$ n is zero, $C_{1-6}$ alkoxycarbonyl, $CO_2H$; $R^a$ is hydrogen; $R^b$ is hydrogen, $C_{1-6}$ alkylsulfonyl, $R^3$ is hydrogen, $C_{1-6}$ alkoxy or $R^3$ and $R^{4a}$ together are $CH_2$—O and together with atoms to which they are attached form a 2,3-duhydrobenzofuran; $R^4$ is $CR^{4a}R^{4b}R^{4c}$ wherein (i) $R^{4a}$, $R^{4b}$ and $R^{4c}$ are $C_{1-3}$ alkyl, or $R^{4a}$ and one of $R^5$ or $R^3$ and together are $CH_2$—O or $(CH_2)_2$ and together with atoms to which they are attached form a 2,3-dihydro-benzofuran, $R^{4b}$ and $R^{4c}$ are $C_{1-3}$ alkyl and the other of $R^5$ or $R^3$ is hydrogen. $R^5$ is hydrogen or $R^5$ and $R^{4a}$ together are $CH_2$—O and together with atoms to which they are attached form a 2,3-dihydrobenzofuran; or, a pharmaceutically acceptable salt thereof.

In another embodiment of the present invention there is provided a compound according to formula I wherein $R^1$ is a heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, and 1,1-dioxo-1$\lambda^6$-isothiazolidin-2-yl wherein the heterocycle is optionally substituted with one or two substitutents independently selected from $C_{1-6}$ alkyl] or halogen; and $R^2$ is —$CR^{2a}$=$CR^{2a}$Ar or —$(C(R^{2b})_2)_n$Ar.

In another embodiment of the present invention there is provided a compound according to formula I wherein $R^1$ is a heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, and 1,1-dioxo-1$\lambda^6$-isothiazolidin-2-yl wherein the heterocycle is optionally substituted with one or two substitutents independently selected from $C_{1-6}$ alkyl] or halogen; $R^2$ is —$CR^{2a}$=$CR^{2a}$Ar, —$(C(R^{2b})_2)_n$Ar; Ar is phenyl substituted at least by substituted at least by $(CH_2)_n NR^a R^b$ at the 4-position wherein n is zero. The phrase "phenyl substituted at least by $(CH_2)_n NR^c R^d$ at the 4-position refers to a substituent of with the formula (i) wherein unsubstituted positions can be further optionally substituted.

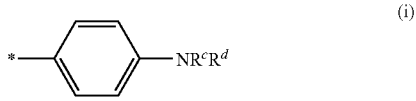

(i)

In another embodiment of the present invention there is provided a compound according to formula I wherein $R^1$ is a heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, and 1,1-dioxo-1$\lambda^6$-isothiazolidin-2-yl wherein the heterocycle is optionally substituted with one or two substitutents independently selected from $C_{1-6}$ alkyl] or halogen; $R^2$ is —$CR^{2a}$=$CR^{2a}$Ar; $R^{2a}$ is hydrogen; $R^3$ is hydrogen or $C_{1-6}$ alkoxy; $R^4$ is trifluoromethyl or $CR^{4a}R^{4b}R^{4c}$ wherein $R^a$, $R^b$ and $R^c$ are methyl; Ar is phenyl substituted at least by substituted at least by $(CH_2)_n NR^a R^b$ at the 4-position wherein n is zero; $R^a$ is $C_{1-6}$ alkylsulfonyl; and $R^b$ is hydrogen.

In a another embodiment of the present invention there is provided a compound according to formula I wherein $R^1$ is a heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, and 1,1-dioxo-1$\lambda^6$-isothiazolidin-2-yl wherein the heterocycle is optionally substituted with one or two substitutents independently selected from $C_{1-6}$ alkyl] or halogen; $R^2$ is —$CR^{2a}$=$CR^{2a}$Ar; $R^{2a}$ is hydrogen; $R^3$ is hydrogen or $C_{1-6}$ alkoxy; $R^4$ is $CR^{4a}R^{4b}R^{4c}$ and $R^a$, $R^b$ and $R^c$ are methyl; and Ar is phenyl substituted at least by substituted at least by $(CH_2)_n NR^a R^b$ at the 4-position wherein n is zero; $R^a$ is $C_{1-6}$ haloalkyl; and $R^b$ is hydrogen.

In yet another embodiment of the present invention there is provided a compound according to formula I wherein $R^1$ is a heterocyclic moiety selected from the group consisting of 2-oxo-tetrahydro-pyrimidin-1-yl, 2-oxo-imidazolin-1-yl, 2,6-dioxo-tetrahydro-pyrimidin-1-yl, 2,5-oxo-imidazolin-1-yl, 2-oxo-piperidin-1-yl, 2-oxo-pyrrolidin-1-yl, and 1,1-dioxo-1$\lambda^6$-isothiazolidin-2-yl wherein the heterocycle is optionally substituted with one or two substitutents independently selected from $C_{1-6}$ alkyl] or halogen; $R^2$ is —$CR^{2a}$=$CR^{2a}$Ar; $R^{2a}$ is hydrogen; $R^3$ is hydrogen or $C_{1-6}$ alkoxy; $R^4$ is $CR^{4a}R^{4b}R^{4c}$ and $R^a$, $R^b$ and $R^c$ are methyl; and Ar is phenyl substituted at least by substituted at least by $(CH_2)_n NR^a R^b$ at the 4-position wherein n is zero; $R^a$ is 2,2,2-trifluoroethyl; and $R^b$ is hydrogen.

In another embodiment of the present invention there is provided a compound according to formula I wherein le is a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl wherein said heteroaryl moiety optionally independently substituted with one or two halogen substituents; and $R^2$ is —$CR^{2a}$=$CR^{2a}$Ar or —$(C(R^{2b})_2)_n$Ar.

In another embodiment of the present invention there is provided a compound according to formula I wherein $R^1$ is a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl wherein said heteroaryl moiety optionally independently substituted with one or two halogen substituents; $R^2$ is —$CR^{2a}$=$CR^{2a}$Ar, —$(C(R^{2b})_2)_n$Ar; Ar is phenyl substituted at least by substituted at least by $(CH_2)_n NR^a R^b$ at the 4-position wherein n is zero.

In another embodiment of the present invention there is provided a compound according to formula I wherein $R^1$ is a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl, wherein said heteroaryl moiety optionally independently substituted with one or two halogen; $R^2$ is —$CR^{2a}$=$CR^{2a}$Ar; $R^{2a}$ is hydrogen; $R^3$ is hydrogen or $C_{1-6}$ alkoxy; $R^4$ is trifluoromethyl or $CR^{4a}R^{4b}R^{4c}$ wherein $R^a$, $R^b$ and $R^c$ are methyl; Ar is phenyl substituted at least by substituted at least by $(CH_2)_n NR^a R^b$ at the 4-position wherein n is zero; $R^a$ is $C_{1-6}$ alkylsulfonyl; and $R^b$ is hydrogen.

In a another embodiment of the present invention there is provided a compound according to formula I wherein $R^1$ is a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl wherein said heteroaryl moiety optionally independently substituted with one or two halogen; $R^2$ is —$CR^{2a}$=$CR^{2a}$Ar; $R^{2a}$ is hydrogen; $R^3$ is hydrogen or $C_{1-6}$ alkoxy; $R^4$ is $CR^{4a}R^{4b}R^{4c}$ and $R^a$, $R^b$ and $R^c$ are methyl; and Ar is phenyl substituted at least by substituted at least by $(CH_2)_n NR^a R^b$ at the 4-position wherein n is zero; $R^a$ is $C_{1-6}$ haloalkyl; and $R^b$ is hydrogen.

In yet another embodiment of the present invention there is provided a compound according to formula I wherein $R^1$ is a heteroaryl moiety selected from the group consisting of 2-oxo-2(H)-pyridin-1-yl, 6-oxo-6H-pyridazin-1-yl, 6-oxo-6H-pyrimidin-1-yl and 2-oxo-2H-pyrazin-1-yl wherein said heteroaryl moiety optionally independently substituted with one or two halogen; $R^2$ is —$CR^{2a}$=$CR^{2a}$Ar; $R^{2a}$ is hydrogen; $R^3$ is hydrogen or $C_{1-6}$ alkoxy; $R^4$ is $CR^{4a}R^{4b}R^{4c}$ and $R^a$, $R^b$ and $R^c$ are methyl; and Ar is phenyl substituted at least by substituted at least by $(CH_2)_n NR^a R^b$ at the 4-position wherein n is zero; $R^a$ is 2,2,2-trifluoroethyl; and $R^b$ is hydrogen.

In another embodiment of the present invention there is provided a compound according to formula I wherein $R^2$ is —$CR^{2a}$=$CR^{2a}$Ar and $R^4$ is $CR^{4a}R^{4b}R^{4c}$ wherein $R^{4a}$ together with one of $R^5$ or $R^3$ are $CH_2$—O or $(CH_2)_2$ and $R^{4a}$ and $R^5$ or $R^3$ together with atoms to which they are attached form a 2,3-dihydro-benzofuran or an indane and $R^{4b}$ and $R^{4c}$ are $C_{1-3}$ alkyl and the other of $R^5$ or $R^3$ is hydrogen in the case of $R^5$ or hydrogen or $C_{1-6}$ alkoxy in the case of $R^3$.

In another embodiment of the present invention there is provided a compound according to formula I wherein $R^2$ is —$CR^{2a}$=$CR^{2a}$Ar and $R^4$ is $CR^{4a}R^{4b}R^{4c}$ and $R^{4a}$ and $R^{4b}$ together are $C_2$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl or $R^{4a}$ and $R^{4b}$ together with the carbon to which they are attached are 3-oxetanyl, or tetrahydrofuran-2-yl and $R^{4c}$ is methyl.

In another embodiment of the present invention there is provided a compound according to formula I wherein $R^2$ is —$CR^{2a}$=$CR^{2a}$Ar and $R^4$ is trifluoromethyl.

In another embodiment of the present invention there is provided a compound selected from I-1 to I-26 of TABLE I.

In another embodiment of the present invention there is provide a method of treating a HCV infection in a patient in need thereof comprising administering a therapeutically effective amount of a compound according to formula I wherein $R^1$, $R^2$, $R^3$, $R^4$ and $R^5$ are as defined herein above.

In another embodiment of the present invention there is provide a method of treating a HCV infection in a patient in need thereof comprising co-administering a therapeutically effective amount of a compound according to formula I wherein $R^1$, $R^2$, $R^3$, $R^4$ and $R^5$ are as defined herein above and at least one immune system modulator and/or at least one antiviral agent that inhibits replication of HCV.

In another embodiment of the present invention there is provide a method of treating a disease caused by HCV in a patient in need thereof comprising co-administering a therapeutically effective amount of a compound according to formula I wherein $R^1$ $R^1$, $R^2$, $R^3$, $R^4$ and $R^5$ are as defined herein above and at least one immune system modulator selected from interferon, interleukin, tumor necrosis factor or colony stimulating factor.

In another embodiment of the present invention there is provide a method of treating a HCV infection in a patient in need thereof comprising co-administering a therapeutically effective amount of a compound according to formula I wherein $R^1$, $R^2$, $R^3$, $R^4$ and $R^5$ are as defined herein above and an interferon or chemically derivatized interferon.

In another embodiment of the present invention there is provide a method of treating a HCV infection in a patient in need thereof comprising co-administering a therapeutically effective amount of a compound according to formula I wherein $R^1$, $R^2$, $R^3$, $R^4$ and $R^5$ are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In another embodiment of the present invention there is provided a method for inhibiting viral replication in a cell by delivering a therapeutically effective amount of a compound of the formula I wherein $R^1$, $R^2$, $R^3$, $R^4$ and $R^5$ are as defined herein above admixed with at least one pharmaceutically acceptable carrier, diluent or excipient.

In another embodiment of the present invention there is provided a composition comprising a compound according to formula I wherein $R^1$, $R^2$, $R^3$, $R^4$ and $R^5$ are as defined herein above with at least one pharmaceutically acceptable carrier, diluent or excipient.

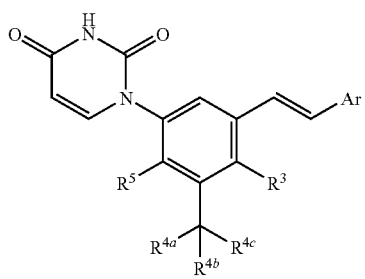

II

In another embodiment of the present invention there is provided a compound according to formula II wherein $R^2$ is —(CH$_2$)$_2$Ar or —CH=CHAr; $R^3$ is hydrogen, $C_{1-6}$ alkoxy, $C_{1-6}$ alkyl, $C_{1-6}$ haloalkyl, $C_{1-6}$ haloalkoxy or halogen, or $R^3$ and $R^{4a}$ together are CH$_2$—O or (CH$_2$)$_2$ and together with atoms to which they are attached form a 2,3-dihydrobenzofuran or an indane; Ar is (a) aryl or (b) heteroaryl wherein said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, $C_{1-3}$ alkoxy-$C_{1-6}$ alkyl, halogen, (CH$_2$)$_n$NR$^a$R$^b$, cyano, $C_{1-6}$ alkoxycarbonyl, carbamoyl, N-alkylcarbamoyl, N,N-dialkylcarbamoyl, (CH$_2$)$_n$CO$_2$H, SO$_2$NH$_2$, $C_{1-6}$ alkylsulfinyl and $C_{1-6}$ alkylsulfonyl; R$^a$ and R$^b$ are independently hydrogen, $C_{1-6}$ alkyl, $C_{1-6}$ haloalkyl, $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, —SO$_2$—NR$^c$R$^d$, $C_{1-3}$ alkylcarbamoyl or $C_{1-3}$ dialkylcarbamoyl; R$^c$ and R$^d$ are (i) independently hydrogen, $C_{1-3}$ alkyl or (CH$_2$)$_{2-6}$NR$^e$R$^f$ or (ii) together with the nitrogen to which they are attached are (CH$_2$)$_2$X$^5$(CH$_2$)$_2$ wherein X$^5$ is O or NR$^i$ and R$^i$ is hydrogen, $C_{1-3}$ alkyl, $C_{1-3}$ acyl or $C_{1-3}$ alkylsulfonyl; R$^e$ and R$^f$ are independently in each occurrence hydrogen or $C_{1-3}$ alkyl; R$^{4a}$ and R$^{4b}$ (i) together are C$_2$ alkylene and R$^{4c}$ is $C_{1-2}$ fluoroalkyl or, (ii) either R$^5$ or R$^3$ and R$^{4a}$ together are CH$_2$—O or (CH$_2$)$_2$ and together with atoms to which they are attached form a 2,3-dihydro-benzofuran or an indane and R$^{4b}$ and R$^{4c}$ are $C_{1-3}$ alkyl; R$^5$ is hydrogen or R$^5$ and R$^{4a}$ together are CH$_2$—O or (CH$_2$)$_2$ and together with atoms to which they are attached form a 2,3-dihydrobenzofuran or an indane; n is independently in each occurrence zero to three; or; a pharmaceutically acceptable salt thereof.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, iert-butyl, tert-butyl, neopentyl, hexyl, and octyl. Any carbon hydrogen bond can be replaced by a carbon deuterium bond with departing from the scope of the invention.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., (CH$_2$)$_n$) or a branched saturated divalent hydrocarbon radical of 2 to 10 carbon atoms (e.g., —CHMe- or —CH$_2$CH (i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 1 2-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "haloalkoxy" as used herein refers to a group —OR where R is haloalkyl as defined herein. The term "haloalkylthio" as used herein refers to a group —SR where R is haloalkyl as defined herein.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "cyano" as used herein refers to a carbon linked to a nitrogen by a triple bond, i.e., —C≡N. The term "nitro" as used herein refers to a group —$NO_2$. The term "carboxy" as used herein refers to a group —$CO_2H$.

The term oxo refers to a doubly bonded oxygen (=O), i.e. a carbonyl group.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl or "alkanoyl" refers to a group —C(=O)R contain 1 to 6 carbon atoms. The $C_1$ acyl group is the formyl group wherein R=H and a C6 acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The term "cyclic amine" as used herein refers to a saturated carbon ring, containing from 3 to 6 carbon atoms as defined above, and wherein at least one of the carbon atoms is replaced by a heteroatom selected from the group consisting of N, O and S, for example, piperidine, piperazine, morpholine, thiomorpholine, di-oxo-thiomorpholine, pyrrolidine, pyrazo line, imidazolidine, azetidine wherein the cyclic carbon atoms are optionally substituted by one or more substituents, selected from the group consisting of halogen, hydroxy, phenyl, lower alkyl, lower alkoxy or 2-hydrogen atoms on a carbon are both replace by oxo (=O). When the cyclic amine is a piperazine, one nitrogen atom can be optionally substituted by $C_{1-6}$ alkyl, $C_{1-6}$ acyl, $C_{1-6}$ alkylsulfonyl.

The terms "alkylsulfonyl" and "arylsulfonyl" as used herein denotes a group of formula —S(=O)$_2$R wherein R is alkyl or aryl respectively and alkyl and aryl are as defined herein. The term $C_{1-3}$ alkylsulfonylamido as used herein refers to a group RSO$_2$NH— wherein R is a $C_{1-3}$ alkyl group as defined herein. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, S(=O)$_2$R wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively.

The terms "alkylsulfonylamido" and "arylsulfonylamido" as used herein denotes a group of formula —NR'S(=O)$_2$R wherein R is alkyl or aryl respectively, R' is hydrogen or $C_{1-3}$ alkyl, and alkyl and aryl are as defined herein.

The terms "alkylsulfinyl" and "arylsulfinyl" as used herein denotes a group of formula —S(=O)R wherein R is alkyl or aryl respectively and alkyl and aryl are as defined herein.

The term "carbamoyl" as used herein means the radical —$CONH_2$. The prefix "N-alkylcabamoyl" and "N,N-dialkylcarbamoyl" means a radical CONHR' or CONR' R" respectively wherein the R' and R" groups are independently alkyl as defined herein. The prefix N-arylcarbamoyl" denotes the radical CONHR' wherein R' is an aryl radical as defined herein.

The term "benzyl" as used herein refers to a $C_6H_5CH_2$ radical wherein the phenyl ring which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylamino alkyl, and dialkylamino alkyl, alkylsulfonyl, arylsulfinyl, alkylamino sulfonyl, arylaminosulfonyl, alkylsulfonylamido, arylsulfonylamido, carbamoyl, alkylcarbamoyl and dialkylcarbamoyl, arylcarbamoyl, alkylcarbonylamino, arylcarbonylamino, unless otherwise indicated.

The term "heteroaryl" as used herein without additional definition or limitation refers to "pyridinyl", "pyrazinyl" and "pyridazinyl" rings. The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered nonfused heteroaromatic ring with two nitrogen atoms disposed in a 1,3, a 1,4 and a 1,2 relationship respectively. The respective radical names are in parentheses.

The terms "oxetane" (oxetanyl), "tetrahydrofuran" (tetrahydrofuranyl) and "tetrahydropyran" (tetrahydropyranyl") refer to a four, five and six-membered non-fused heterocyclic ring respectively, each containing one oxygen atom.

The term "aryl" as used herein without further limitation refers to phenyl or naphthyl.

The terms (i) 2-oxo-tetrahydro-pyrimidin-1-yl, (ii) 2-oxo-imidazolin-1-yl, (iii) 2,6-dioxo-tetrahydro-pyrimidin-1-yl, (iv) 2,5-oxo-imidazolin-1-yl, (v) 2-oxo-piperidin-1-yl, (vi) 2-oxo-pyrrolidin-1-yl, and (vii) 1,1-dioxo-1$\lambda^6$-isothiazolidin-2-yl, refer to the following moieties:

(i) 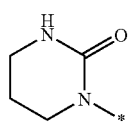

(ii) 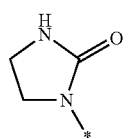

(iii) 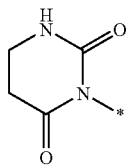

(iv) 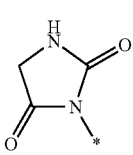

(v) 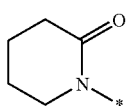

(vi) 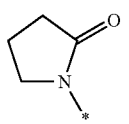

(vii) 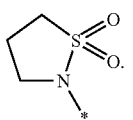

The terms (viii) 2-oxo-2(H)-pyridin-1-yl, (ix) 6-oxo-6H-pyridazin-1-yl, (x) 6-oxo-6H-pyrimidin-1-yl and (xi) 2-oxo-2H-pyrazin-1-yl refer to the following moieties:

(viii) 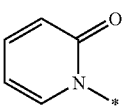

(ix) 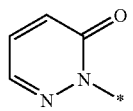

(x) 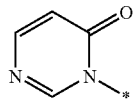

(xi) 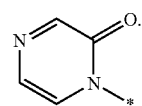

To avoid ambiguity, the following nomenclature and numbering systems are used: 1-oxo-1H-isochromen-1-one (A), 2H-isoquinolin-1-one (B), benzooxazol-2-yl (C). benzothiaol-2-yl (D) and dihydrobenzofuran (E).

A 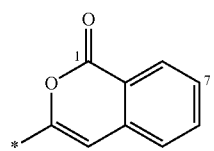

B 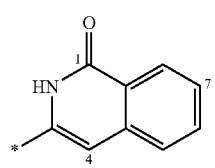

C 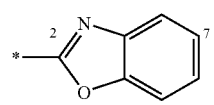

D 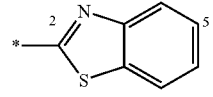

E 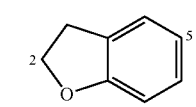

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and anti-infective compounds. Such combination therapy may also comprise providing a compound of the invention either concurrently or sequentially with other medicinal agents or potentiators, such as ribavirin and related compounds, amantadine and related compounds, various interferons such as, for example, interferon-α, interferon-β, interferonγ and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristol Myers Squibb), and ITMN-191 (Intermune).

Examples of the interferons include, but are not limited to pegylated rIFN-α 2b, pegylated rIFN-α 2a, rIFN-α 2b, rIFN-α 2a, consensus IFNα (infergen), feron, reaferon, intermax alpha, r-IFN-beta, infergen and actimmune, IFN-omega with DUROS, albuferon, locteron, Albuferon, Rebif, oral interferon α, IFNα-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride (BOC2O), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe$_2$Si (TBDMS), triethylamine (TEA or Et$_3$N), triflate or CF$_3$SO$_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I
| Cpd. No. | | IC$_{50}$[1] (μM) | mp | ms |
|---|---|---|---|---|
| I-1 | 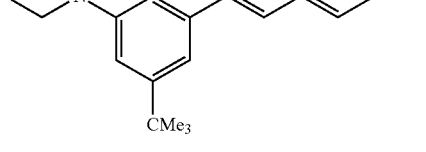 | 0.015[2] | 235.0-237.0 | 428 |
| I-2 | 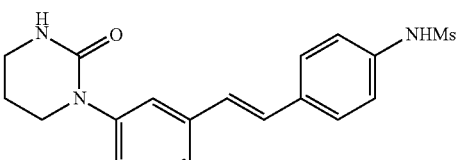 | 0.010 | | 458 |
| I-3 | 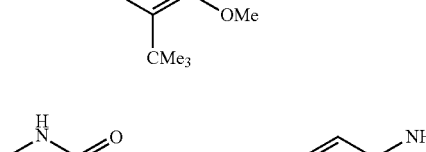 | 0.013[2] | 244.0-246.0 | 460 |
| I-4 | 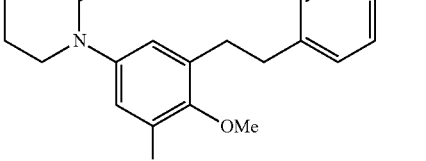 | 0.032[2] | 229.0-231.0 | 446 |
| I-5 | 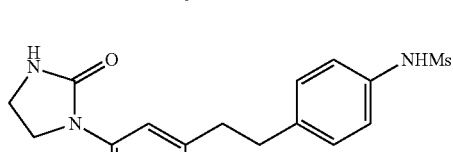 | 0.001 | | 486 |
| I-6 | 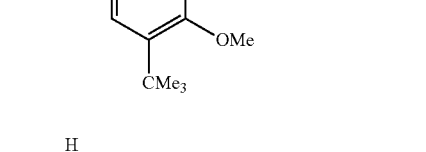 | 0.063 | | 474 |

TABLE I-continued

| Cpd. No. | Structure | IC$_{50}$[1] (μM) | mp | ms |
|---|---|---|---|---|
| I-7 | | 0.015 | 230.0-231.0 | 460 |
| I-8 | | 0.016 | 247.0-249.0 | 457 |
| I-9 | | 0.001 | 254.0-256.0 | 453 |
| I-10 | | 0.005 | 248.0-250.0 | 471 |
| I-11 | | 0.00038 | 260.0-262.0 | 454 |
| I-12 | | 0.001 | 202.0-204.0 | 454 |

TABLE I-continued

| Cpd. No. | Structure | IC$_{50}$$^1$ (μM) | mp | ms |
|---|---|---|---|---|
| I-13 | | 0.00031 | 214.0-216.0 | 454 |
| I-14 | | 000042 | | 498 |
| I-15 | | 0.001 | | 512 |
| I-16 | | 0.00039 | 176.0-179.0 | 498 |
| I-17 | | 0.00049 | 238.0-240.0 | 484 |
| I-18 | | 0.005 | | 404 |
| I-19 | | 0.002 | | 405 |

TABLE I-continued

| Cpd. No. | Structure | $IC_{50}^{1}$ ($\mu M$) | mp | ms |
|---|---|---|---|---|
| I-20 | | 0.083 | 83.0-86.0 | 481 |
| I-21 | | 0.00023 | 275.0-278.0 | 502 |
| I-22 | | 0.003 | 272.0-275.0 | 496 |
| I-23 | | 0.00037 | 285-288 | 484 |
| I-24 | | 0.0633 | | 473 |
| I-25 | | $0.019^{2}$ | 211.0-212.0 | 474 |

TABLE I-continued

| Cpd. No. | | IC$_{50}$[1] (μM) | mp | ms |
|---|---|---|---|---|
| I-26 | (structure) | 0.0051 | 255.0-257.0 | 494 |
| I-27 | (structure) | 0.0003 | 289-291 | 457 |

[1] HCV Polymerase Assay
[2] 20 nm cIRES

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can be varied to afford the various compounds contemplated in this invention. Moreover, the reaction conditions are exemplary and alternative conditions are well known. The reaction sequences in the following examples are not meant to limit the scope of the invention as set forth in the claims.

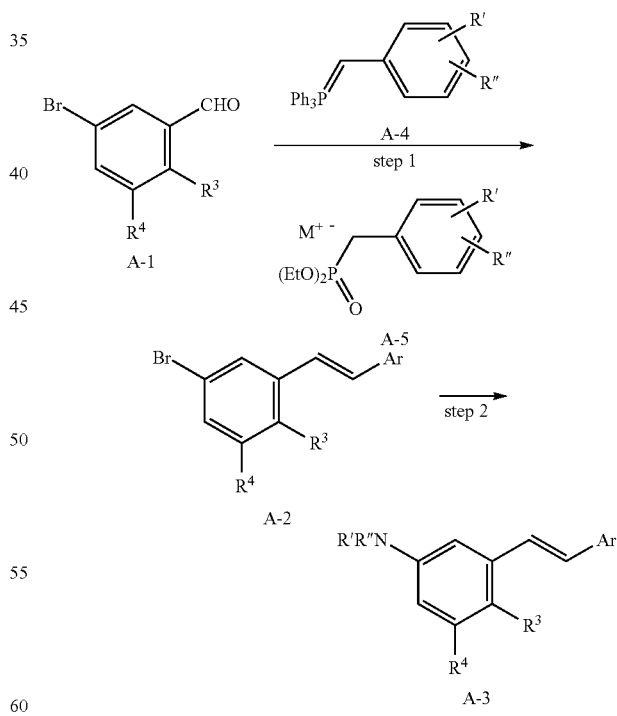

Compounds of general formula I within the scope of the current claims are characterized by an aryl ring with an N-linked optionally substituted heterocyclic ring or an optionally substituted heteroaryl ring as defined herein above as the R$^1$ substituent. 3-Halo-benzaldehydes (or a benzaldehyde with a functionally equivalent leaving group such as trifluorosulfonyloxy substitutent) are useful precursors that permit the stepwise elaboration of the $R^1$ and $R^2$ substituents. Alternately meta dihalo benzene derivatives are amenable to similar strategy employing alternative synthetic methodology as described below. (SCHEME B).

Appropriately substituted m-bromobenzaldehyde derivatives including, but not limited to, 5-bromo-3-(1,1-dimethylethyl)-2-methoxy-benzaldehyde (A-1, $R^3$=OMe, $R^4$=CMe$_3$, CASRN 417717-87-8) or 5-bromo-3-(1,1-dimethylethyl)-benzaldehyde (A-1, $R^3$=H, $R^4$=CMe$_3$, CASRN 241155-85-1) are useful precursors to compounds within the scope of the invention. The styryl side chain can be introduced by a Wittig condensation with a benzylidene-$\lambda^5$-phosphane (A-4) or a Wadsworth-Horner-Emmons condensation with the conjugate base of a diethyl benzyl-phosphonate (A-5) to afford A-2. The preparation of aryl substituted analogs is readily accomplished using aryl substituted benzyl halides. Diethyl (4-nitro-benzyl)phosphonate is a suitable precursor for compounds of the present invention substituted with an amine which can, in turn, be optionally sulfonylated. Selective reduction of the nitro group can be carried out with a variety of well-known reducing agents. For example an activated metal such as activated iron, zinc or tin (produced for example by washing iron powder with a dilute acid solution such as dilute hydrochloric acid). Concomitant reduction of the nitro substituent and the olefinic or acetylenic linker is easily accomplished by catalytic hydrogenation affording (4-amino-phenyl)-ethyl derivatives which are HCV polymerase inhibitors or which can be used as intermediates to other compounds of formula I within the scope of the invention The Wittig reaction is the reaction of an aldehyde or ketone with a triphenyl phosphonium ylide to afford an alkene and triphenylphosphine oxide. (A. Maercker, *Org. React.* 1965, 14, 270-490; A. W. Carruthers, Some Modern Methods of Organic Synthesis, Cambridge University Press, Cambridge, UK, 1971, pp 81-90) Wittig reactions are most commonly used to couple aldehydes and ketones to singly substituted phosphine ylides. The Wittig reagent is usually prepared from a phosphonium salt, which is in turn made by the reaction of Ph$_3$P with an alkyl halide. To form the Wittig reagent (ylide), the phosphonium salt is suspended in a solvent such as Et$_2$O or THF and a strong base such as phenyl lithium or n-butyl lithium is added. With simple ylides, the product is usually mainly the Z-isomer, although a lesser amount of the E-isomer also is often formed. This is particularly true when ketones are used. If the reaction is performed in DMF in the presence of LiI or NaI, the product is almost exclusively the Z-isomer. If the E-isomer is the desired product, the Schlosser modification may be used. With stabilized ylides (phosphonate carbanions) the product is mainly the E-isomer. Alternatively The Horner-Wadsworth-Emmons reaction (B. E. Maryanoff and A. B. Reitz, *Chem. Rev.* 1989 89:863-927) is the chemical reaction of stabilized phosphonate carbanions with aldehydes (or ketones) to produce predominantly E-alkenes. The Horner-Wadsworth-Emmons reaction (or HWE reaction) is the condensation of stabilized phosphonate carbanions with aldehydes (or ketones) to produce predominantly E-alkenes. In contrast to phosphonium ylides used in the Wittig reaction, phosphonate-stabilized carbanions are more nucleophilic and more basic.

Compounds wherein $R^2$ is an ((E)-styryl)-phenyl moiety also be prepared by condensation of substituted toluene derivatives with al aldehyde such as 32b. This is most practical when toluene is substituted with electronegative groups which increase the acidity of protons on the methyl group and allow deprotonation of the methyl and addition to the aldehyde to afford a carbinol that undergoes subsequent dehydration. (see e.g., example 9)

Methodology for efficient amination of aryl halides has been extensively investigated. The conversion of an aryl halide to aniline can be accomplished a palladium-catalyzed amination with benzophenone imine with Pd(OAc)$_2$ or Pd$_2$(dba)$_3$ in the presence of BINAP and a basic additive such as NaO-tert-Bu or Cs$_2$CO$_3$. (J. P. Wolfe et al., *Tetrahedron Lett.* 1997 38(36):6367-70) and followed by hydrolysis of the imine. Direct amination with ammonia also has been reported. (D. S. Surry and S. L. Buchwald, *J. Am. Chem. Soc.* 2007 129(34):100354)

The primary amine can subsequently be converted to lactams such as pyrrolidones and piperidones by acylation of the amine with a 2-bromo-propanoic acid or 3-bromo-butyric acid derivatives and subsequent cyclization by intramolecular displacement of the halide to afford the lactam. Acylation is accomplished by established procedures using activated intermediates, acid chlorides or acid anhydrides. One skilled in the art will appreciate the availability of a variety of substituted halo acids which can be used analogously.

The primary amine can subsequently be converted to 2,4-dioxo-dihydro-pyrimidin-3-yl and 2,4-dioxo-imidazolidin-3-yl substituents by acylation with 3-chloro-propyl isocyanate or 2-chloro-ethyl isocyanate respectively. Condensation of the isocyanate radical with the primary amine affords a urea which is subsequently cyclized to the targeted heterocycles.

A complementary procedure for aryl amination exploits CuI catalyzed amination of an aryl halide with an amine or diamine in the presence of proline and a base such as K$_2$CO$_3$. (D. Ma et al. *Organic Lett.* 2003 5(14):2453-55) The primary amine can subsequently be converted to 2-oxo-imidazolidin-1-yl and 2-oxo-tetrahydro-pyrimidin-1-yl radicals. Condensation of the aryl amine with 1,3 diamino-propane and cyclization of the resulting diamine with carbonyl diimidazole affords the 2-oxo-tetrahydro-pyrimidin-1-yl radical.

Alternatively the primary amine can be subjected to reductive amination with a N-protected α-amino-aldehyde or β-amino-aldehyde. Reductive amination is preferably carried out carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7. Removal of the protecting group affords a diamine which can be cyclized with CDI. One skilled in the art will recognize that substituted amino aldehydes are readily available from α amino acids which afford substituted imidazolidines and tetrahydropyrimidines.

Compounds of general formula I wherein $R^1$ is an N-linked heteroaryl moiety such as a 2-oxo-2(H)-pyridin-1-yl, 6-oxo-6H-pyridazin-1-yl, 6-oxo-6H-pyrimidin-1-yl and 2-oxo-2H-pyrazin-1-yl were prepared by CuI amination of an aryl halide by 1H-pyridin-2-one, 2H-pyridazin-3-one, 3H-pyrimidin-4-one and 1H-pyrazin-2-one respectively.

Alternatively the benzaldehyde derivative can be homologated to produce an acetylene (e.g., see example 3). Nitration and methylation of 3-tert-butyl-2-hydroxy-benzaldehyde afford 42b which was reacted with diethyl (1-diazo-2-oxopropyl)-phosphonate under basic conditions to afford an acetylene. This sequence illustrates the introduction of the nitrogen by electrophilic nitration of the aryl ring. Palladium-catalyzed coupling utilizing the Sonogashira conditions affords a diarylacetylene which can be subjected to catalytic reduction to simultaneously reduce the nitro group to the amine and the acetylene to an ethyl linker. Elaboration of the N-linked heterocyclic substituent is carried out as described above.

The Sonogashira coupling (K. Sonogashira et al., *Tetrahedron Lett.* 1975 4467-4470; K. Sonogashira, *Comprehensive Organic Synthesis*; B. M. Trost and I. Fleming Eds.; Pergamon Press, Oxford, 1991; Vol. 3, Chapter 2.4, p 521) is a cross-coupling aryl or vinyl halide (or triflate) and a terminal alkyne. Typically carried out in the presence of a palladium catalyst, for example $PdPh_4$ or $PdPh_2Cl_2$ and the like, and a cuprous salt, for example CuI, a dialkyl- or trialkylamine such as diethylamine, diisopropylamine, triethylamine and the like at temperature from RT to 100° C. The reaction can be carried out using the amine base as the solvent or with other organic solvents including hydrocarbons, ethers, alcohols, aqueous DMA and the like.

SCHEME B

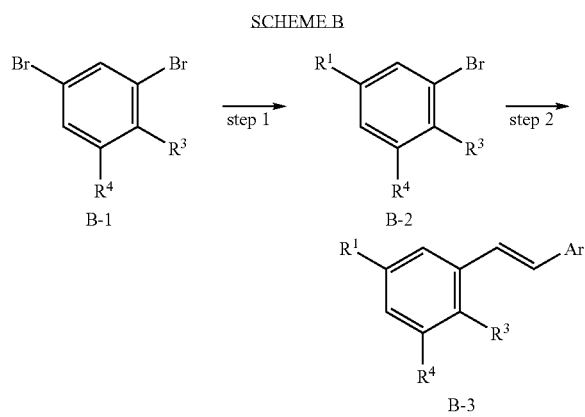

Compounds of general formula I can also be prepared from dihalides of formula B-1 by a stepwise introduction of the N-linked amine substituent and elaboration of the $R^2$ group which can be accomplished by a palladium-catalyzed coupling (e.g., example 13 and 16). While SCHEME B depicts the sequential introduction of the amine then the styryl moiety, on skilled in the art will appreciate that the relative reactivity of the two leaving groups is effected by the nature of the leaving groups and electronic and steric perturbations arising from other substituents and therefore it may be desirable to reverse the sequence. introduction of the $R^1$ substituent can be accomplished by the previously noted reactions.

Introduction of the $R^2$ substituent when the precursor is a dihalide is typically accomplished using a Suzuki reaction other a variant thereof such as the Stille reaction. Thus, for example in the sequence depicted in example 13 the styryl side chain is introduce by a Suzuki reaction with B-[(1E)-2-[4-[(methylsulfonyl)amino]phenyl]ethenyl]boronic acid. Boronate esters such as N-{4-[(E)-2-(4,4,6-trimethyl-[1,3,2] dioxaborinan-2-yl)-vinyl]-phenyl}-methanesulfonamide (example 15) also are useful.

The Suzuki reaction is a palladium-catalyzed coupling of a boronic acid ($R-B(OH)_2$) wherein R is aryl or vinyl) with an aryl or vinyl halide or triflate (R'Y wherein R'=aryl or vinyl; Y=halide or $-OSO_2CF_3$) o afford a compound R—R'. Typical catalysts include $Pd(PPh_3)_3$, $Pd(OAc)_2$ and $PdCl_2(dppf)$. With $PdCl_2(dppf)$, primary alkyl borane compounds can be coupled to aryl or vinyl halide or triflate without β-elimination. Highly active catalysts have been identified (see, e.g. J. P. Wolfe et al., *J. Am. Chem. Soc.* 1999 121(41):9550-9561 and A. F. Littke et al., *J. Am. Chem. Soc.* 2000 122(17):4020-4028). The reaction can be carried out in a variety of organic solvents including toluene, THF, dioxane, 1,2-dichloroethane, DMF, DMSO and acetonitrile, aqueous solvents and under biphasic conditions. Reactions are typically run from about room temperature to about 150° C. Additives (e.g. CsF, KF, TlOH, NaOEt and KOH) frequently accelerate the coupling. There are a large number of parameters in the Suzuki reaction including the palladium source, ligand, additives and temperature and optimum conditions sometimes require optimization of the parameters for a given pair of reactants. A. F. Littke et al., supra, disclose conditions for Suzuki cross-coupling with arylboronic acids in high yield at RT utilizing $Pd_2(dba)_3/P(tert-bu)_3$ and conditions for cross-coupling of aryl- and vinyl triflates utilizing $Pd(OAc)_2/P(C_6H_{11})_3$ at RT. J. P. Wolf et al., supra, disclose efficient condition for Suzuki cross-coupling utilizing $Pd(OAc)_2\%$-(di-tert-butylphosphino)biphenyl or o-(dicyclohexylyphosphino)biphenyl. One skilled in the art can determine optimal conditions without undue experimentation.

The Stille cross-coupling reaction is a palladium-catalyzed coupling of an aryl or vinyl stannanes with aryl or vinyl halides or -sulfonyloxy compounds (J. K. Stille *Angew. Chem. Int. Ed.* 1986 25:508-524; A. F. Littke and G. C. Fu *Angew. Chem. Int. Ed.* 1999, 38:2411-2413). Commercially available Pd reagents including $Pd(PPh_3)_4$, $Pd(OAc)_2$ and $Pd_2(dba)_3$ can be used. Phosphine ligands are useful rate accelerants if they ar not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al. *J. Org. Chem.* 1994 59:5905-5911). The reaction is typically run in aprotic solvents at elevated temperature. Reagents such as 1-{butyl-[(E)-2-(dibutyl-propyl-stannanyl)-vinyl]-propyl-stannanyl}-butane permit stepwise construction of a diaryl-ethene two sequential Stille condensations.

Compounds of general formula I wherein $R^4$ is a substituted cyclopropane are readily prepared from precursors such as, but not limited to, 3,5-dibromo-benzeneacetonitrile (CASRN 188347-48-0) or 3,5-dibromo-2-methoxy-benzeneacetonitrile (CASRN 75098-07-6). Dialkylation of an arylacetonitrile with 1,2-dibromoethane is a general procedure to elaborate the cyclopropane ring (see, e.g., example 14). The nitrile can then be reduced to the corresponding aldehyde and subsequently converted to a difluoroalkyl or hydroxymethyl substitutent. Hydrolysis of the nitrile affords the carboxylic acid which can be subjected to the Kochi reaction (J. K. Kochi et al. *J. Am. Chem. Soc.* 1965 87(11):2500-2502) to afford the chloro-cyclopropane. Palladium-catalyzed cross-coupling with a boronic acid and amination will afford compounds of general formula I.

The dihydrobenzofuran scaffold was constructed by a intra-molecular free-radical cyclization of an ortho-(2-methyl-allyloxy)-bromo benzene (see, e.g., example 15). Dihalogenation of the resulting 3,3-dimethyl-dihydro-benzofuran affords a dihalide which can be subjected to palladium-catalyzed cross-coupling and amination. The corresponding indane is available from 4,6-dibromo-7-methoxy-indan-1-one (CASRN125714-97-8). The gem-dimethyl center is introduced by additional of methyl Grignard followed by $Ti(IV)Cl_4/ZnMe_2$ mediated replacement of the tertiary alcohol. The resulting dibromide can be converted to compounds of general formula I by the procedures described previously. Compounds of general formula II are prepared analogously but the amination is carried out as described in example 13.

Compounds of the present invention with an isochromene substituent on the phenyl ring were prepared by a gold-catalyzed cycloisomerization of acetylenic acids and esters (E. Genin et al., *J. Am. Chem. Soc.* 2006 128(10):3112-3113). Methyl 2-phenylethynyl-benzoates undergo $AuCl_3$-mediated 6-endo cyclization to directly afford the desired isochromen-1-ones C-1. (E. Marchal et al., *Tetrahedron* 2007 63:9979-9990) Thus, the $AuCl_3$ catalyzed cyclization of $C_{1-2}$ afforded C-1.

intramolecular cycloisomerization to afford the desired 2H-isoquinolin-1-ones D-2 occurred.

Anti-Viral Activity

The activity of the inventive compounds as inhibitors of HCV activity may be measured by any of the suitable meth-

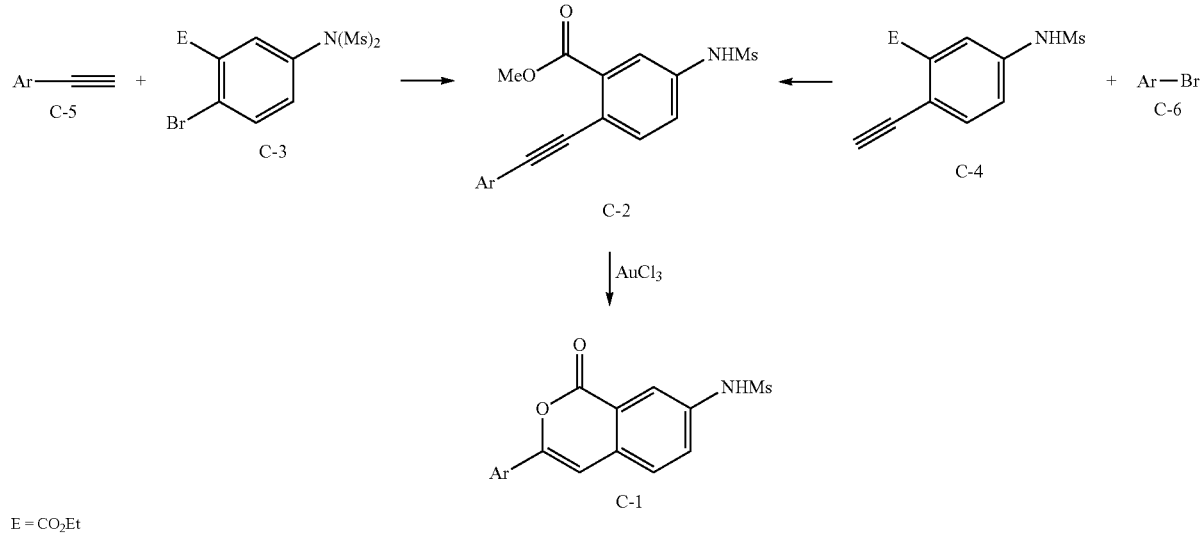

SCHEME C

E = CO₂Et

The requisite acetylenic esters were prepared by a Sonogashira coupling of a suitable substituted aryl halide $C_{1-6}$ and an optionally substituted alkyl ortho-ethynyl-benzoate (C-4). As will be apparent to one skilled in the art, the acetylene can originate on either of the aryl residues.

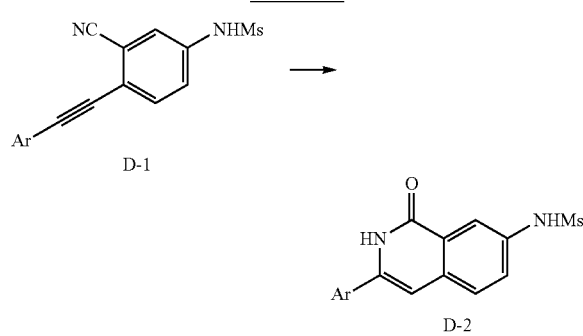

SCHEME D

Compounds encompassed in the present claims wherein the aryl ring is substituted by a 2H-isoquinolin-1-one were prepared by a related intramolecular cyclization of the corresponding cyano-acetylene (SCHEME B). Hydrolysis of the nitrile (D-1) in the presence of hydrido(dimethylphosphinous acid-kP)[hydrogen bis(dimethylphosphnito-kP]platinum (II) (CASRN 173416-05-2; X-b Jiang et al., Platinum-Catalyzed Selective Hydration of Hindered Nitriles and Nitriles with Acid- or Base Sensitive Groups, *J. Org. Chem.* 2004 69(7): 2327-31; T. Ghaffar and A. W. Parkins, A New Homogenous Platinum Containing Catalyst for the Hydrolysis of Nitriles. *Tetrahedron Lett.* 1995 36(47):8657-8660), induced an ods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 8. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The term "treatment" of a HCV infection, as used herein, also includes treatment of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

N-(4-{(E)-2-[3-tert-Butyl-5-(2-oxo-tetrahydro-pyrimidin-1-yl)-phenyl]-vinyl}-phenyl)-methanesulfonamide (I-1)

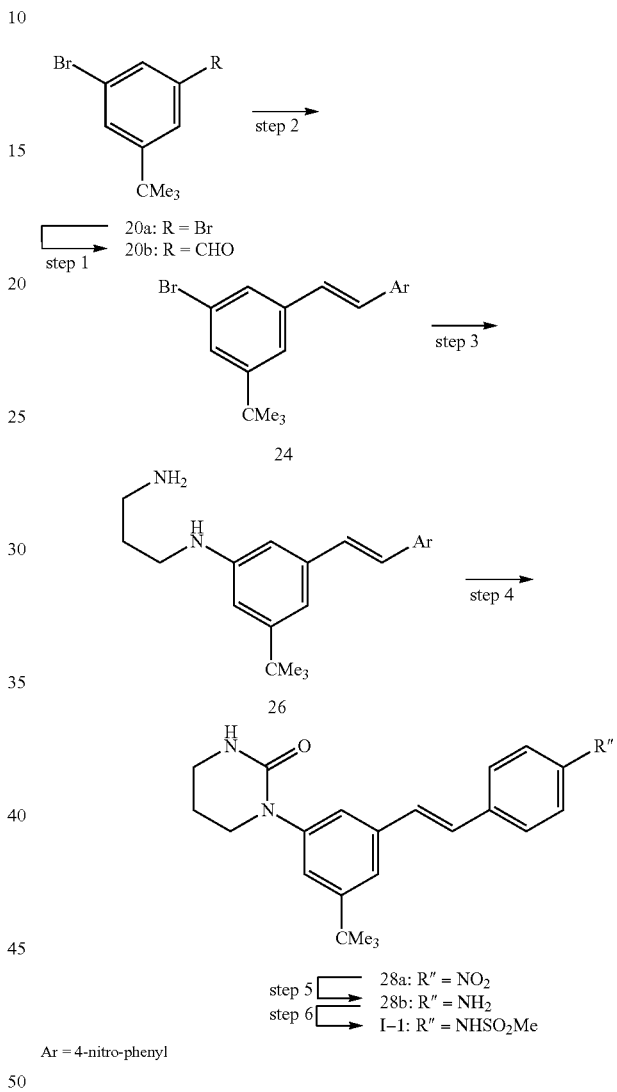

Ar = 4-nitro-phenyl step 1—To a solution of 20a (3.9 g, 13.3 mmol) and Et$_2$O cooled to −78° C. under an Ar atmosphere was added slowly a solution of n-BuLi (5.8 mL, 14.6 mmol, 2.5 M solution in hexane) and the pale yellow solution was stirred at −78° C. for 1.5 h. To this solution was added DMF (2.1 mL, 26.6 mmol). The reaction was quenched with H$_2$O (10 mL), thrice extracted with Et$_2$O and combined extracts was washed with brine, dried (MgSO$_4$), filtered and concentrated in vacuo to afford 3.9 g (100%) of 20b as an oil.

step 2—To a solution of 15-crown-5 (0.3 mL, 1.6 mmol) and THF cooled to 0° C. and maintained under an Ar atmosphere was added diethyl 4-nitrobenzyl-phosphate (4.8 g, 17.7 mmol) and the red solution was stirred at 0° C. for 10 min, then a solution of 20b (3.9 g, 16.1 mmol) and THF was added and the reaction stirred at RT for 72 h. The reaction was quenched with sat'd. aq. NH$_4$Cl (40 mL) the resulting solution thrice extracted with EtOAc. The combined extracts were washed with brine, dried (MgSO₄), filtered and evaporated. The crude product was purified by SiO₂ chromatography eluting with an EtOAc/hexane gradient (0 to 5% EtOAc) to afford 1.6 g (27%) of 24 as a yellow solid.

step 3—To a solution of 24 (1.6 g, 4.4 mmol) and DMSO under Ar in a vial was added sequentially proline (0.092 g, 0.8 mmol), K₃PO₄ (1.6 g, 8 mmol), CuI (0.075 g, 0.4 mmol) followed by 1,3-diamino-propane (0.440 g, 8 mmol). The vial was sealed and heated to 150° C. overnight. The crude mixture was loaded directly onto an SiO₂ column, and eluted with an EtOAc/hexane gradient (50% EtOAc to 100% EtOAc to 100% 60:10:1 DCM:MeOH:NH₄OH) to afford 0.750 g of 26. "Solution A" as used in this specification refers to a 60:10:1 mixture of DCM:MeOH:NH₄OH.

step 4—To a solution 26 (0.150 g, 0.39 mmol) and THF was added carbonyl diimidazole (0.070 g, 0.43 mmol) and the resulting solution heated at reflux for 2 h. The solution was cooled to RT and concentrated in vacuo. The crude product was purified by SiO₂ chromatography eluting with a DCM/ 60:10:1 DCM:MeOH:NH₄OH gradient (95 to 25% DCM) to afford 190 mg (100%) of 28a.

step 5—To a suspension of 28a (190 mg, 0.50 mmol) in 3:1 EtOH/H₂O was added NH₄Cl (70 mg) and iron powder (70 mg, 1.2 mmol) and the resulting solution heated at reflux for 1 h. The solution was cooled to RT and filtered through glass filter paper and the solid washed with EtOAc. The filtrate was washed with brine, dried (MgSO₄), filtered and concentrated in vacuo to afford 110 mg of 28b (63%) as an orange solid.

step 6—To a solution of 28b (110 mg, 0.31 mmol) dissolved in DCM and cooled to 0° C. was added pyridine (75 μL, 0.93 mmol) and mesyl chloride. The reaction was allowed to warm to RT and stirred overnight. The solution was concentrated and loaded unto a SiO₂ column eluting with a DCM/ 60:10:1 DCM:MeOH:NH₄OH gradient (95 to 66% DCM) to afford 54 mg (40%) of I-1 as a solid: mp=235.0-237.0° C.; ms (M+H)⁺=350.

Example 2

N-(4-{(E)-2-[3-tert-Butyl-2-methoxy-5-(2-oxo-tetrahydro-pyrimidin-1-yl)-phenyl]-vinyl}-phenyl)-methanesulfonamide (I-2)

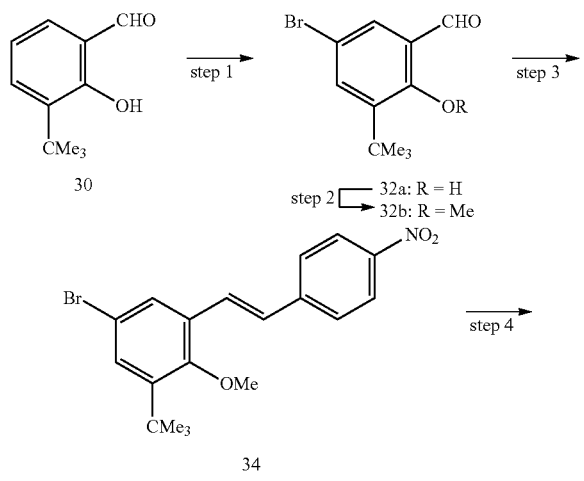

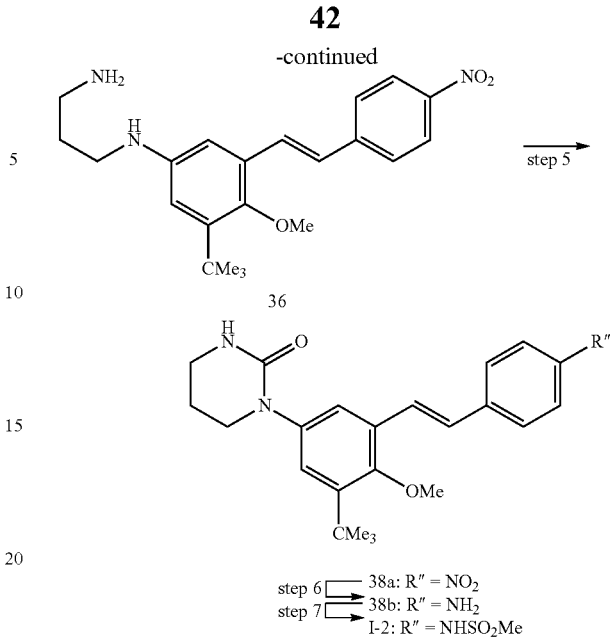

step 1—To a solution of 30 (5.00 g, CASRN 24623-65-2) and DCM (20 mL) at 0° C. was added dropwise a solution of Br₂ (1.45 mL) in DCM (15 mL) over a period of 30 min. After the addition was complete the reaction was stirred for 1 h then the organic volatiles were removed under reduced pressure to afford 7.23 g of 32a as a light yellow solid.

step 2—A mixture of 32a (3.83 g), MeI (2.32 mL) and K₂CO₃ (6.18 g) in DMF (50 mL) was heated at 50° C. for 1 h then cooled to RT and diluted with ether and water. The organic layer was thrice washed with water then brine, dried (MgSO₄), filtered and concentrated to afford 3.99 g of 32b as a yellow solid.

step 3: Sodium hydride (0.10 g, 2.6 mmol, 60% dispersion) and 15-crown-5 (0.038 g, 0.17 mmol) were added to THF (5 mL) at 0° C. and stirred for 5 min. To the reaction mixture was then added dropwise over 5 min, a solution of diethyl (4-nitrobenzyl)phosphonate (0.52 g, 1.9 mmol) in THF (5 mL) and stirring was continued at 0 C for 5 min. To the reaction mixture was then added dropwise over 10 min a solution of 32b (0.47 g, 1.7 mmol) in THF (10 mL). The reaction mixture was stirred for 30 min at 0° C. then for 90 min at RT. Water was carefully added, and the mixture was partitioned between water and EtOAc. The EtOAc layer was washed sequentially with water and brine, dried (Na₂SO₄), filtered and concentrated. The crude residue was purified by SiO₂ chromatography eluting with EtOAc/hexane to afford 0.67 g (94%) of 34 as a yellow solid (0.67 g, 94%).

step 4—To a solution of 34 (500 mg, 1.2 mmol) and DMSO under Ar in a vial was added sequentially proline (0.030 g, 0.25 mmol), K₃PO₄ (0.54 g, 10 mmol), CuI (0.024 g, 0.5 mmol) followed by 1,3-diamino-propane (0.140 g, 1.9 mmol). The vial was sealed and heated to 150° C. overnight. The crude mixture was taken-up in EtOAc (60 mL), washed with water and brine, dried (MgSO₄) and concentrated to 450 mg of 36 (91%).

step 5—To a solution 36 (0.450 g, 1.1 mmol) and THF was added carbonyl diimidazole (0.190 g, 0.1.1 mmol) and the resulting solution heated at reflux for 18 h. The solution was cooled to RT, taken-up in DCM, and purified by SiO₂ chromatography eluting with a EtOAc/hexanes (5% to 20% to 100% EtOAc followed by a DCM/60:10:1 DCM:MeOH: NH₄OH gradient (95 to 25% DCM) to afford 300 mg (73%) of 38a.

step 6—To a suspension of 38a (300 mg, 0.73 mmol) in EtOH/H$_2$O (3:1) was added NH$_4$Cl (100 mg) and iron powder (100 mg). The mixture was heated at reflux for 1 h. The reaction mixture was cooled to RT and filtered through a glass filter paper. The filtrate was diluted with EtOAc (60 mL), washed with brine (20 mL), dried (MgSO$_4$), filtered and concentrated in vacuo. The crude product was purified by SiO$_2$ chromatography eluting with a stepwise gradient (33% EtOAc/hexane, 100% EtOAc and 100% 60:10:1 DCM:MeOH:NH$_4$OH) to afford 110 mg (39%) of 38b as an oil.

step 7—To a solution of 38b (0.180 g, 0.47 mmol) in DCM cooled to 0° C. was added pyridine (0.1 mL, 1.47 mmol) and mesyl chloride (35 µL, 0.47 mmol) The solution was stirred for 1.5 h than directly applied to a SiO$_2$ column (40-80 g) and eluted with a stepwise gradient (25% EtOAc/hexane, 100% EtOAc and 100% "magic solvent"). The recovered material was rechromatographed on SiO$_2$ and eluted with DCM/"60:10:1 DCM:MeOH:NH$_4$OH" to afford 11 mg (5%) of I-2: MS (M+H)$^+$=458.

Example 3

N-(4-{2-[3-tert-Butyl-2-methoxy-5-(2-oxo-tetrahydro-pyrimidin-1-yl)-phenyl]-ethyl}-phenyl)-methanesulfonamide (I-3)

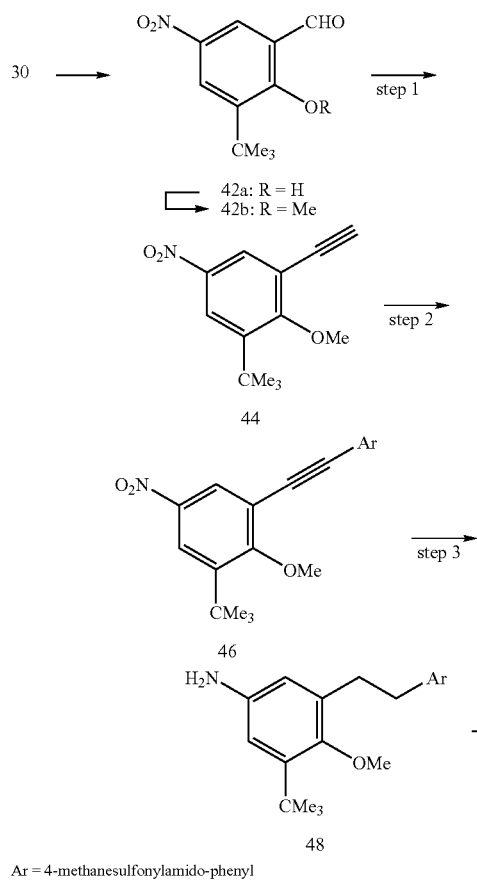

Ar = 4-methanesulfonylamido-phenyl step 1—To a solution of 42b (0.981 g, 4.14 mmol, CASRN 107342-30-3) cooled to −78° C. was added sodium methoxide (17 mL, 8.5 mmol, 0.5 M solution in NaOMe) followed by a solution of diethyl (1-diazo-2-oxo-propyl)-phosphonate (10.105 g, 6.21 mmol) in MeOH (8 mL). The solution was gradually warmed to RT and stirred overnight. The reaction was quenched with satd. aq. NaHCO$_3$ then concentrated in vacuo. The residue was diluted with EtOAc, washed sequentially with sat'd. aq. NaHCO$_3$, water and brine. The combined extracts were dried (Na$_2$SO$_4$), filtered and concentrated in vacuo. The crude product was purified by SiO$_2$ chromatography eluting with an EtOAc/hexane gradient (0 to 3% EtOAc) to afford 0.851 g (88%) of 44 as a colorless oil.

step 2—A solution of 44 (0.101 g, 0.433 mmol), N-(iodophenyl)-methansulfonamide (0.255 g, 0.859 mmol), PdCl$_2$(PPh$_3$)$_2$ (15 mg, 0.021 mmol), CuI (0.010 g, 0.053 mmol), EtOH (3 mL) and THF (3 mL) was stirred overnight at RT under an Ar atmosphere. The reaction was then heated to 60° C. for 3 h. An additional aliquot of PdCl$_2$(PPh$_3$)$_2$ (17 mg) was added and heating was continued overnight. The crude reaction mixture was concentrated and the crude product was purified by SiO$_2$ chromatography eluting with an EtOAc/hexane gradient (20 to 30% EtOAc) to afford 47 mg of 46.

step 3—A mixture of 46, Pd(OH)$_2$ (116 mg), MeOH (5 mL) and EtOAc (5 mL) was hydrogenated in a Parr shaker at 45 psi. After 5 h the flask was evacuated and the catalyst removed by filtration. The filtrate was returned to the Parr, an additional 75 mg of Pd(OH)$_2$ was added and the hydrogenation continued for 2 h (50 psi H$_2$). The catalyst was filtered and the filtrated concentrated and the residue purified by SiO$_2$ chromatography eluting with an EtOAc/hexane gradient (10 to 50% EtOAc) to afford 83 mg of 48.

step 4—A solution of 3-chloro-propyl isocyanate in THF (4 mL) was stirred at RT overnight. To the resulting solution was added EtOH (3 mL), H$_2$O (3 mL) and KOH (135 mg) and the resulting solution was heated at 80° C. for 5 h. The reaction mixture was cooled to RT, concentrated in vacuo and diluted with EtOAc. The solution was made acidic with 1 N HCl and the organic phase removed, dried (Na$_2$SO$_4$), filtered and concentrated in vacuo. The crude product was purified on a preparative SiO$_2$ TLC plate developed with EtOAc to afford 39.9 mg (39%) of I-3.

I-4 was prepared analogously except in step 6,3-chloropropyl isocyanate was replaced with 2-chloro-ethyl isocyanate. The product was purified on a preparative SiO$_2$ TLC plate developed with 2:1 EtOAc/hexane.

Example 4

N-(4-{(E)-2-[3-tert-Butyl-5-(4,4-dimethyl-2-oxo-tetrahydro-pyrimidin-1-yl)-2-methoxy-phenyl]-vinyl}-phenyl)-methanesulfonamide (I-5)

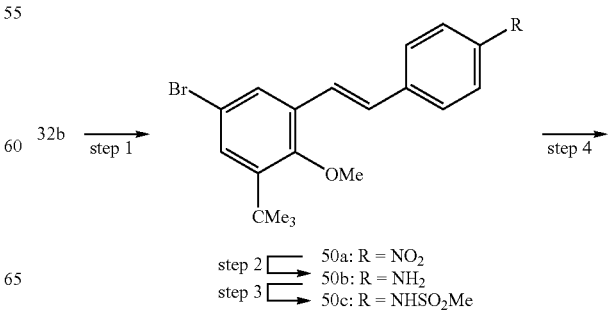

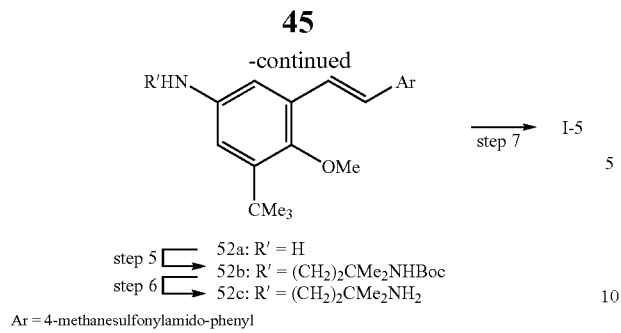

step 5 ⟶ 52a: R' = H
step 6 ⟶ 52b: R' = (CH$_2$)$_2$CMe$_2$NHBoc
         52c: R' = (CH$_2$)$_2$CMe$_2$NH$_2$ Ar = 4-methanesulfonylamido-phenyl step 1—Condensation of 32b and diethyl (4-nitro-benzyl)-phosphonate was carried in accord with the procedure in step 3 of example 1. The crude product was purified by SiO$_2$ chromatography eluting with 5% EtOAc/hexane to afford 2.70 g (98%) of 50a.

step 2—Reduction of 50a was carried out in accord with the procedure in step 5 of example 1. The crude product was used without further purification.

step 3—The conversion of 50b to the sulfonamide 50c in accord with the procedure described in step 6 of example 1.

step 4—A flask was charged with 50c (1.00 g, 2.283 mmol), benzophenone imine (0.625 g, 3.724 mmol), Pd$_2$(dba)$_3$ (108 mg, 0.118 mmol), BINAP (0.211 g, 0.339 mmol), NaO-tert-Bu (0.486 g, 5.057 mmol) and degassed with vacuum-Ar cycles. Toluene (20 mL) was added and the resulting solution heated at 80° C. overnight. The reaction was cooled and additional aliquots of Pd$_2$(dba)$_3$ (97 mg) and BINAP (140 mg) were added and heated continued overnight. The reaction mixture was cooled and filtered through CELITE® and the filtrate concentrated. The residue was dissolved in MeOH (20 mL) and 50% aq. NH$_2$OH (4 mL) was added and the reaction mixture was stirred overnight at RT. The crude product was purified by SiO$_2$ chromatography eluting with an EtOAc/hexane gradient (50 to 75% EtOAc) and the partially purified fractions pooled and rechromatographed on a SiO$_2$ column with a stepwise EtOAc/hexane gradient (10, 25 and 40% EtOAc) to afford 695 mg of 52a as an orange oil.

step 5—To a solution of 52a (0.311 mg, 0.832 mmol), tert-butyl (1,1-dimethyl-3-oxopropyl)carbamate (0.205 g, 1.020 mmol, CASRN 181646-38-8) and DCE (10 mL) was added HOAc (3 drops) and the resulting solution stirred at RT for 75 min. To the resulting solution was added NaBH(OAc)$_3$ (0.352 g 1.661 mmol) and the solution stirred overnight at RT. The reaction was quenched with sat'd. aq. NaHCO$_3$ and stirred for 1 h. The organic phase was separated, dried (Na$_2$SO$_4$), filtered and evaporated. The crude product was purified by SiO$_2$ chromatography eluting with an EtOAc/hexane gradient (10 to 25% EtOAc) to afford 0.253 g (54%) of 52b.

step 6—To a solution of 52b (0.085 g, 0.152 mmol) and DCM (5 mL) cooled to 0° C. was added TFA (60 μL) and the reaction stored in a freezer for 72 h. The reaction mixture, which had proceeded to ca. 30% conversion was warmed to RT and an additional TFA (120 μL) added and stirring continued for 24 h. Finally an additional 20 μL of TFA was added and stirred for an additional 1 h. The reaction mixture was diluted with DCM and washed with sat'd. aq. NaHCO$_3$, dried (Na$_2$SO$_4$), filtered and evaporated to afford 66 mg (95%) of 52c which was used without additional purification.

step 7—A solution of 52c (66 mg, 0.144 mmol), CDI (0.107 g, 0.660 mmol) and THF (10 mL) was heated overnight at reflux. The solution was cooled, concentrated and diluted with EtOAc. The solution was twice washed with H$_2$O, dried (Na$_2$SO$_4$), filtered and evaporated. The crude product was purified on a preparative SiO$_2$ TLC plate developed with 2:1 EtOAc/hexane and the crude product rechomatographed with the same solvent to afford 12.3 mg (18%) of I-5

Example 5

N-(4-{2-[3-tert-Butyl-5-(2,6-dioxo-tetrahydro-pyrimidin-1-yl)-2-methoxy-phenyl]-ethyl}-phenyl)-methanesulfonamide (I-6)

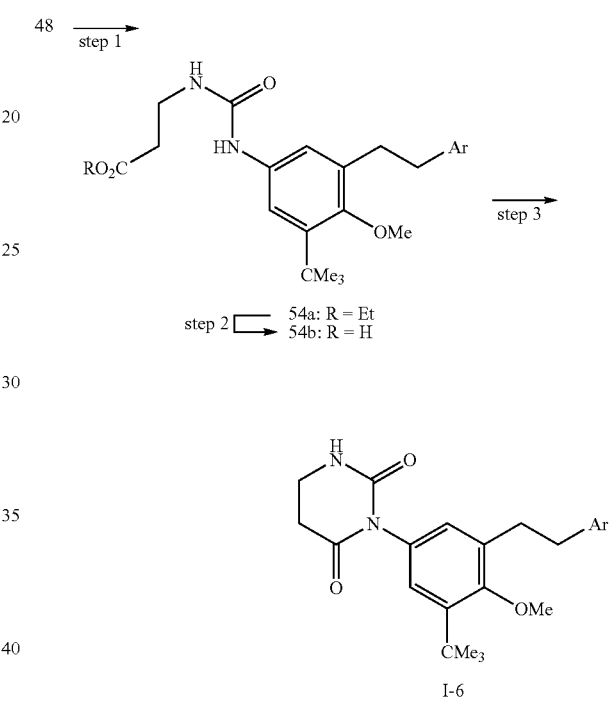

Ar = 4-methanesulfonylamido-phenyl step 1—A solution of 48 (0.100 g, 0.266 mmol) and ethyl 3-isocyanatopropanoate (40 μL, 0.304 mmol, CASRN 5100-34-5) in THF (5 mL) was stirred overnight. The reaction mixture was concentrated and purified by SiO$_2$ chromatography eluting with an EtOAc/hexane gradient to afford 0.085 g (63%) of 54a as a solid.

step 2—To a solution of 54a (0.112 g, 0.216 mmol) in THF (5 mL) and H$_2$O (5 mL) was added powdered KOH (0.121 g) and the resulting solution stirred for 2 h at RT. The reaction mixture was concentrated and partitioned between EtOAc and HCl. The organic phase was dried (Na$_2$SO$_4$), filtered and concentrated to afford 0.80 g (75%) of 54b as a tan solid.

step 3—A solution of 54b (80 mg, 0.163 mmol), con HCl (1.5 mL) and toluene (15 mL) was heated overnight at 120° C. in a flask fitted with a Dean-Stark trap. The reaction was cooled to RT, concentrated and the crude product was purified on a preparative TLC plate developed with 2:1 EtOAc/hexane to afford 11.7 mg of I-6.

Example 6

N-(4-{2-[3-tert-Butyl-5-(2,5-dioxo-imidazolidin-1-yl)-2-methoxy-phenyl]-ethyl}-phenyl)-methanesulfonamide (I-7)

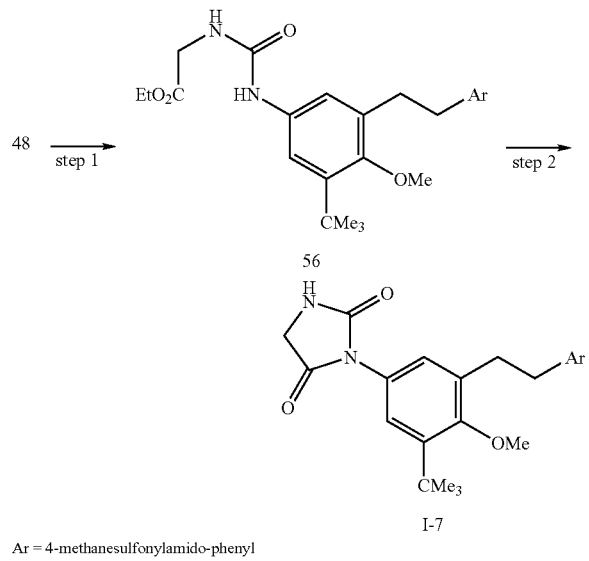

Ar = 4-methanesulfonylamido-phenyl step 1—Condensation of 48 and ethyl 4 isocyanatoacetate (CASRN 2949-22-6) to afford 56 was carried out in accord with step 1 of example 5.

step 2—To a solution of 56 in THF (15 mL) cooled to 0° C. was added NaH (45 mg). The reaction was stirred for 1 h. The reaction appeared about 50% complete. The reaction was warmed to RT and stirred for 3 h. An additional aliquot of NaH (35 mg) was added and stirring continued overnight. The reaction mixture was quenched with 1N HCl (4 mL) and diluted with EtOAc. The EtOAc solution was washed with brine, dried ($Na_2SO_4$), filtered and evaporated. The crude product was purified on a preparative $SiO_2$ TLC plate developed with 2:1 EtOAc/hexane, then dried and rerun with 4:1 EtOAc/hexane. The less polar band was eluted and rechromatographed on a plate with 1:1 EtOAc/hexane to afford 18.7 mg (15%) of I-7 as an off white solid.

I-25 was prepared analogously except in step 1, ethyl 4 isocyanatoacetate was replaced with ethyl 2-isocyanato-propanoate (CASRN 13794-28-0).

Example 7

N-(4-{(E)-2-[3-tert-Butyl-2-methoxy-5-(2-oxo-piperidin-1-yl)-phenyl]-vinyl}-phenyl)-methanesulfonamide (I-8)

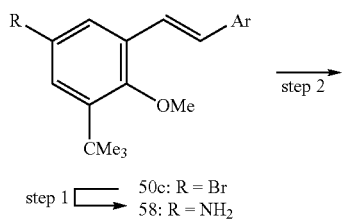

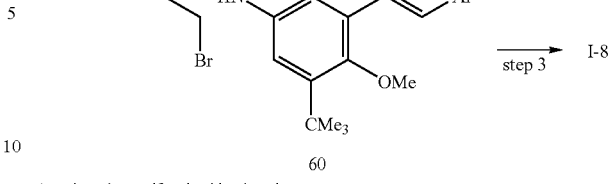

Ar = 4-methanesulfonylamido-phenyl step 1—Amination of 50c was carried out with benzophenone imine and $Pd_2(dba)_3$ in accord with step 4 of example 4 to afford 58.

step 2—To a solution of 58 (0.127 g, 0.340 mmol), TEA (50 µL) and DCM cooled to 0° C. was added 4-bromo-butyryl chloride (100 µL, 0.373 mmol) and the reaction mixture was stirred for 2.5 h. Water was added and the organic phase separated and washed with sat'd. aq. $NaHCO_3$ and brine. The organic phase was dried ($Na_2SO_4$), filtered and concentrated in vacuo to afford 178 mg (96%) of 60.

step 3—To a solution of 60 (0.176 g, 0.328 mmol) and DMF (10 mL) cooled to 0° C. was added NaH (56 mg, 60% mineral oil dispersion) and the solution was warmed to RT and stirred overnight. LCMS indicated there was partial conversion to product. An additional aliquot of NaH (46 mg) was added and stirring continued. The reaction was quenched with $H_2O$ and extracted with EtOAc. The organic phase was washed with 1N HCl then twice with brine. The extract was dried ($Na_2SO_4$), filtered and concentrated in vacuo to afford 136 mg of crude product. The crude product was purified on a preparative $SiO_2$ TLC plate developed with 2:1 EtOAc/hexane to afford 19.5 mg of I-8 as a white solid.

N-(4-{(E)-2-[3-tert-Butyl-2-methoxy-5-(2-oxo-pyrrolidin-1-yl)-phenyl]-vinyl}-phenyl)-methanesulfonamide can be prepared analogously except in step 2,4-bromo-butyryl chloride is replaced with 3-bromo-propionyl chloride.

Example 8

N-(4-{(E)-2-[3-tert-Butyl-2-methoxy-5-(2-oxo-2H-pyridin-1-yl)-phenyl]-vinyl}-phenyl)-methanesulfonamide (I-9)

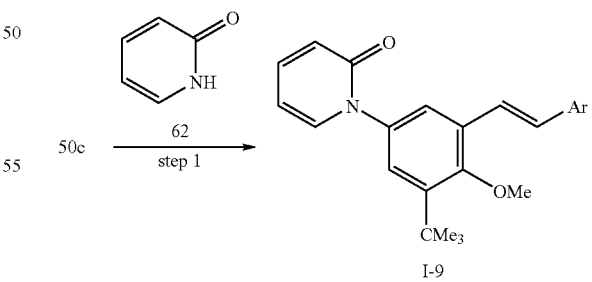

Ar = 4-methanesulfonylamido-phenyl

A vial was charged with 50c (250 mg, 0.576 mmol), 1H-pyridin-2-one (82 mg, 0.863 mmol), CuI (0.11 mg), $K_2CO_3$ (236 mg), 4,7-dimethoxy-[1,10]phenanthroline (21 mg, CASRN 92149-07-0) and DMSO (2 mL), sealed and irradiated in a microwave synthesizer to 150° C. for 5 h. The reaction was cooled to RT and partitioned between EtOAc and H₂O. The organic phase was separated, dried (MgSO₄), filtered and concentrated in vacuo. The crude product was purified by SiO₂ chromatography eluting with an EtOAc/hexane gradient to afford 0.128 g of I-9.

The following were prepared analogously except 2-hydroxy-pyridine was replaced by the compound in parenthesis: I-10 (5-fluoro-2(1H)pyridone), I-11 (3(2H)-pyridazinone, CASRN 504-30-3), I-12 (4(3H)-pyrimidinone CASRN 4562-27-0), I-13 (2(1H)pyridazinone, CASRN 6270-63-9)

Example 9

2-{(E)-2-[3-tert-Butyl-2-methoxy-5-(2-oxo-2H-pyrazin-1-yl)-phenyl]-vinyl}-5-methanesulfonylamino-benzoic acid methyl ester (I-15)

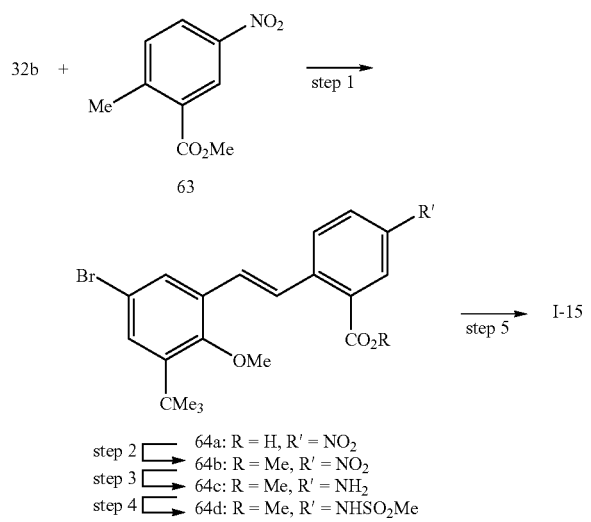

step 1—A solution of 32b (4.17 g, 15.39 mmol), 63 (2.00 g, 10.26 mmol), DBU (3.1 mL, 20.73 mmol) and DMSO (10 mL) was stirred overnight at RT then heated to 50° C. for 1 h. To the solution was added 1N NaOH and the resulting solid filtered. The filtrate was acidified with 6N HCl extracted with EtOAc and the combined extracts dried (Na₂SO₄), filtered and evaporated to afford 2.51 g of 64a.

step 2—A solution of 64a (2.00 g, 4.608 mmol) iodomethane (1.05 mL, 16.87 mmol), K₂CO₃ (1.92 g, 13.89 mmol) and DMF (10 mL) was stirred overnight at RT. The resulting solution was filtered and the filtrate was diluted with EtOAc and washed sequentially with 1N HCl, H₂O and brine. The organic phase was dried (Na₂SO₄), filtered and concentrated in vacuo to afford 1.94 g (94%) of 64b.

step 3—To a solution of 64b (1.42 g, 3.18 mmol) in DMF (10 mL) and EtOAc (10 mL) was added SnCl₂ (2.87 g, 12.72 mmol) and the resulting solution stirred at RT overnight. The reaction mixture was cooled to 0° C. and quenched by slow addition of aq. NaHCO₃ (4 mL). The resulting suspension was filtered through a pad of CELITE and the filtrate diluted with EtOAc, thrice washed with brine, dried (Na₂SO₄), filtered and concentrated in vacuo. The crude product was purified by SiO₂ chromatography eluting with a EtOAc/hexane gradient (10 to 20% EtOAc) to afford 843 mg (64%) of 64c as a yellow foam.

step 4—The methanesulfonamide was prepared by treatment of 64c with mesyl chloride in accord with the procedure in step 6 of example 1. The crude product was purified by SiO₂ chromatography eluting with a EtOAc/hexane gradient (10 to 30% EtOAc) to afford 697 mg (704%) of 64d.

step 5—The palladium-catalyzed coupling of 64d to afford I-15 is carried out in accord with the procedure in example 8 except 62 was replaced with 1H-pyrazin-2-one.

A mixture I-15 (0.28 mmol) and 1N aq. LiOH (1.5 mL) in THF (2 mL), MeOH (2 mL) and H₂O (2 mL) is heated at 70° C. for 5 h. The reaction mixture is cooled to RT and the organic volatiles are removed in vacuo. The aqueous layer is cooled to 0° C. and acidified with 1 N aq. HCl to ca. pH 6.5 and the resulting white precipitate is collected by suction filtration and dried to afford I-16 as a white solid. The filtrate is further extracted with EtOAc. The organic layer is washed with H₂O, brine, dried (MgSO₄), filtered and concentrated to afford additional I-16.

Example 10

N-(4-{(E)-2-[3-tert-Butyl-2-methoxy-5-(2-oxo-2H-pyrazin-1-yl)-phenyl]-vinyl}-3-hydroxymethyl-phenyl)-methanesulfonamide (I-17)

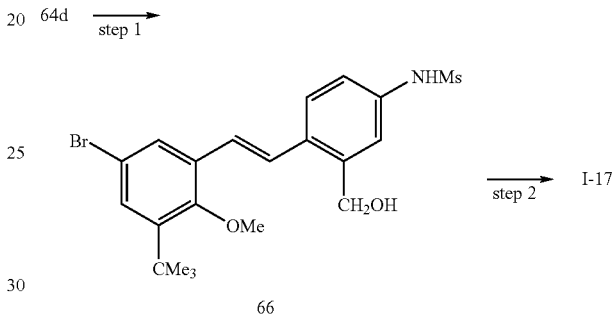

step 1—To a solution of 64d (0.500 g, 1.00 mmol) in THF (10 mL) cooled to 0° C. was added LiBH₄ (70 mg) and the resulting solution allowed to stir at RT overnight. The reaction still contained 64d and an addition aliquot of LiBH₄ (60 mg) was added and stirring continued overnight. A third aliquot of LiBH₄ was added and the reaction heated to 50° C. for 2 h. The reaction was cooled to 0° C. and quenched with sat'd. aq. NaHCO₃ and extracted with EtOAc. The combined extracts were dried (Na₂SO₄), filtered and evaporated. The crude product was purified by SiO₂ chromatography eluting with an EtOAc/hexane gradient (20 to 50% EtOAc) to afford 261 mg of N-{4-[(E)-2-(5-bromo-3-tert-butyl-2-methoxyphenyl)-vinyl]-3-hydroxymethyl-phenyl}-methanesulfonamide (66).

step 2—The palladium-catalyzed coupling of 66 to afford I-17 is carried out in accord with the procedure in example 8 except 62 was replaced with 1H-pyrazin-2-one.

Example 11

N-(4-{(E)-2-[3-tert-Butyl-2-methoxy-5-(2-oxo-2H-pyrazin-1-yl)-phenyl]-vinyl}-3-methoxymethyl-phenyl)-methanesulfonamide (I-14)

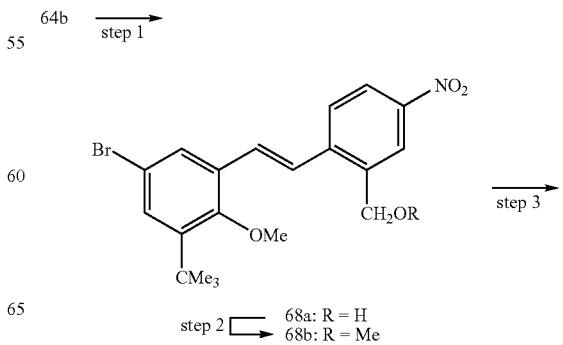

51

-continued

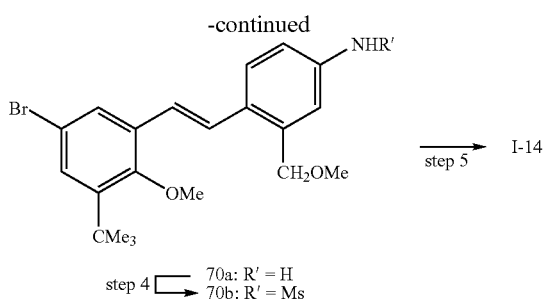

step 4 ⎡ 70a: R' = H
       ⎣ 70b: R' = Ms step 1—To a solution of 64a (1.41 g, 3.15 mmol) and THF (40 mL) cooled to 0° C. was added LiBH₄ (0.206 g, 9.46 mmol) and the resulting solution was allowed to stir overnight at RT. The reaction mixture was cooled to 0° C. and quenched by adding sat'd. aq. NH₄Cl. The solution was extracted with EtOAc and the combined extracts washed with brine, dried (Na₂SO₄), filtered and concentrated in vacuo to afford 0.96 g (72%) of 68a as a yellow solid.

step 2—To a solution of 68a (1.344 g, 3.2 mmol) and DMF (15 mL) cooled to 0° C. was added NaH (0.276 g, 60% mineral oil dispersion). The solution was stirred for 20 min and iodomethane was added (500 µL, 8.03 mmol). The solution was stirred at RT for 2.25 h then recooled to 0° C. and quenched with brine. The resulting solution was extracted with EtOAc and the combined extracts twice washed with brine, dried (Na₂SO₄), filtered and concentrated in vacuo to afford 1.47 g of 68b as a yellow oil which did not require further purification.

step 3—To a solution of 68b (1.389 g, 3.20 mmol) in EtOAc (20 mL) and DMF (20 mL) was added SnCl₂.2H₂O (2.91 g) and the resulting solution was stirred at RT overnight. The solution was cooled to 0° C. and the reaction quenched with sat'd. aq. NaHCO₃. The resulting suspension was filtered through CELITE® and the filtrate thrice washed with brine, dried (Na₂SO₄), filtered and concentrated in vacuo to afford 1.6 of 70a containing small amounts of DMF.

Conversion of the amine to the sulfonamide 70b was carried out in accord with the procedure described in step 6 of example 1. The copper-catalyzed coupling of 70b to afford I-14 is carried out in accord with the procedure in example 8 except 62 was replaced with 1H-pyrazin-2-one.

Example 12

2-{(E)-2-[3-tert-Butyl-2-methoxy-5-(2-oxo-2H-pyrazin-1-yl)-phenyl]-vinyl}-benzoic acid (I-17)

step 1—A solution of methyl 2-bromomethyl-benzoate (9.99 g, 43.6 mmol) and triethylphosphite (7.25 g, 43.6 mmol) was heated to 150° C. for 5 h. The reaction mixture as cooled to RT then purified by SiO₂ chromatography to afford 11.55 g of 2-(diethoxy-phosphorylmethyl)-benzoic acid methyl ester (72)

step 2—A flask was charged with NaH (0.74 g, 60% mineral oil dispersion), blanketed with argon and the solid dispersion thrice washed with hexane then suspended in THF (100 mL). The suspension was cooled to 0° C. and 15-crown-5 (0.34 g, 1.75 mmol) and 72 (4.88 g, 17.0 mmol) were added and the solution stirred for 15 min. To the resulting mixture was added a solution of 32b (4.20 g, (1.55 mmol) and THF (10 mL) and the reaction mixture stirred at 0° C. for 15 min the warmed to RT and stirred overnight. The reaction was quenched with H₂O, concentrated and the residue partitioned between H₂O and EtOAc. The aqueous phase was twice extracted with EtOAc and the combined organic extracts washed with H₂O, dried (Na₂SO₄), filtered and concentrated in vacuo. The crude product was purified by SiO₂ chromatography eluting with an EtOAc/hexane gradient (4 to 40% EtOAc) to afford 3.79 g of ethyl 2-[(E)-2-(5-bromo-3-tert-butyl-2-methoxy-phenyl)-vinyl]-benzoate (74)

step 3—2-{(E)-2-[3-tert-butyl-2-methoxy-5-(2-oxo-2H-pyrazin-1-yl)-phenyl]-vinyl}-benzoic acid methyl ester (76) was prepared by palladium-catalyzed coupling of 74 and 1H-pyrazin-2-one in accord with the procedure in example 8.

step 4—A solution of 76 (0.260 g, 0.6 mmol), NaOH (0.8 mL, 4.0M NaOH solution) and MeOH (6.0 mL) was heated at 70° C. for 4 h. The solution was cooled to 0° C., diluted with H₂O (15 mL) and the pH adjusted to ca. 1 with 6M HCl. The resulting precipitate was filtered and dried at 70° C. in a vacuum oven to afford 0.198 g of I-17 as a tan solid.

I-18 was prepared analogously except in step 3, 1H-pyrazin-2-one was replaced with 1H-pyridin-2-one.

Example 13

N-(4-{(E)-2-[7-(2,4-Dioxo-3,4-dihydro-2H-pyrimidin-1-yl)-4-methoxy-3,3-dimethyl-2,3-dihydro-benzo furan-5-yl]-vinyl}-phenyl)-methanesulfonamide (I-23)

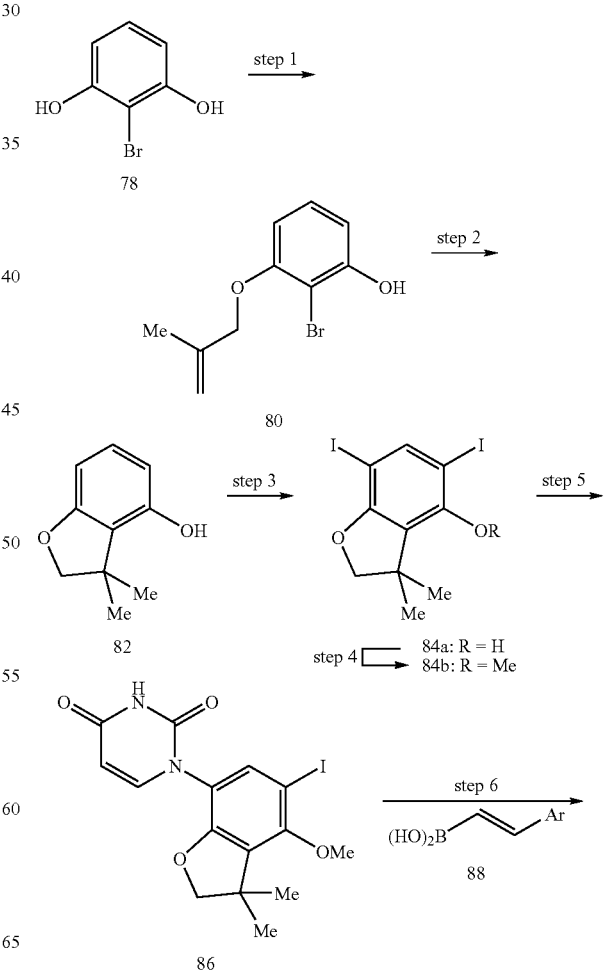

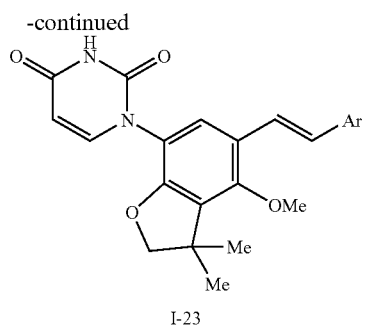

I-23

Ar = 4-methansulfonamido-phenyl step 1—To a solution of 78 (5.512 g, 28 mmol), $K_2CO_3$ (3.128 g, 23 mmol) and acetone (60 mL) was added 3-bromo-2-methyl-propene (1.90 mL, 19 mmol) and the resulting mixture was heated at reflux overnight. The reaction mixture was cooled to RT and concentrated in vacuo. The residue was partitioned between EtOAc and 1M HCl. The aqueous layer was separated and extracted with EtOAc and the combined organic extracts were washed with brine, dried ($Na_2SO_4$), filtered and concentrated in vacuo. The crude product was purified by $SiO_2$ chromatography eluting with an EtOAc/hexane gradient (0 to 10% EtOAc) to afford 2.57 g (56.12%) of 80 as a light yellow oil.

step 2—To a solution of 80 (1.0 g, 4 mmol) and benzene (45 mL) was added sequentially $Bu_3SnH$ (1.839 g, 6 mmol) and AIBN (0.068 g, 0.4 mmol) and the resulting solution was heated at reflux overnight. The reaction mixture was cooled to RT and 10% aq. KF was added and the resulting solution stirred vigorously for 2 h. The phases were separated and the aqueous phase was extracted with EtOAc. The combined organic extracts were washed with brine, dried ($Na_2SO_4$), filtered and concentrated in vacuo. The crude product was purified by $SiO_2$ chromatography eluting with an EtOAc/hexane gradient (0 to 10% EtOAc) to afford 0.602 g (89%) of 82 as a white solid.

step 3—A round-bottom flask was charged with $I_2$ (3.091 g, 12 mmol) and EtOH (40 mL) and then $Ag_2SO_4$ (3.798 g, 12 mmol) and 82 (1.00 g, 6 mmol) were added sequentially. The resulting mixture was stirred at RT for 2 h. The suspension was filtered through CELITE® and the pad was rinsed with EtOAc/EtOH. The filtrate was evaporated and the crude product purified by $SiO_2$ chromatography eluting with an EtOAc/hexane gradient to afford 1.710 g of 84a as a yellow oil.

step 4—To a solution of 84a (1.710 g, 4 mmol) and DMF (12 mL) was added $K_2CO_3$ (1.42 g, 10 mmol) and iodomethane (0.817 g, 6 mmol) and the resulting mixture stirred overnight at RT. The reaction mixture was quenched with $H_2O$ and extracted with $Et_2O$. The aqueous layer was separated and re-extracted with $Et_2O$. The combined extracts were thrice washed with $H_2O$ and once with brine, dried ($Na_2SO_4$), filtered and concentrated in vacuo to afford 1.747 g of 84b as a yellow solid.

step 5—A dry 3-necked round-bottom flask was charged with 84b (0.400 g, 1 mmol), uracil (0.125 g, 1 mmol), N-(2-cyanophenyl)picolinamide (0.042 g, 0.19 mmol), $K_3PO_4$ (0.415 g, 2 mmol) and dry DMSO (6 mL). The flask was evacuated and filled with Ar and Ar was slowly bubbled through the suspension for 20 min. To the mixture was added CuI (0.018 g, 0.09 mmol) and the resulting mixture stirred at 80° C. overnight. The reaction was cooled to RT and poured into $H_2O$ (20 mL) and the pH adjusted to ca. 3 by addition of 2M HCl. The resulting solution was twice extracted with EtOAc and extract was washed with $H_2O$, sat'd. aq. $NH_4Cl$ (20 mL) and brine (20 mL). The combined extracts were dried ($Na_2SO_4$), filtered and concentrated in vacuo. The crude product was purified by $SiO_2$ chromatography eluting with an EtOAc/hexane gradient (0 to 50% EtOAc) to afford 50 mg (13%) of 86 as a white solid.

step 6—A microwave vial was charged with 86 (0.048 g, 0.116 mmol), 88 (0.039 g, 0.16 mmol, CASRN 1132942-08-5), Pd(PPh$_3$)$_4$ (0.013 g), $K_2CO_3$ (0.037 g, 0.35 mmol), MeOH (1.4 mL) and toluene (0.7 mL). The tube was flushed with Ar, sealed and irradiated in a microwave synthesizer at 120° C. for 60 min. The mixture was cooled and partitioned between DCM and sodium acetate buffer adjusted to pH 4.6. The aqueous phase was separated and extracted with DCM. The combined organic extracts were dried ($Na_2SO_4$), filtered and concentrated in vacuo. The crude product was purified by $SiO_2$ chromatography eluting with an EtOAc/hexane gradient (0 to 80% EtOAc) to afford a brown solid which was triturated with $Et_2O$/EtOAc/heptane (1:1:1) to afford 20 mg (52%) of I-23 as a brown powder.

Example 14

N-(4-{(E)-2-[3-(1-Difluoromethyl-cyclopropyl)-2-methoxy-5-(2-oxo-2H-pyridin-1-yl)-phenyl]-vinyl}-phenyl)-methanesulfonamide (100)

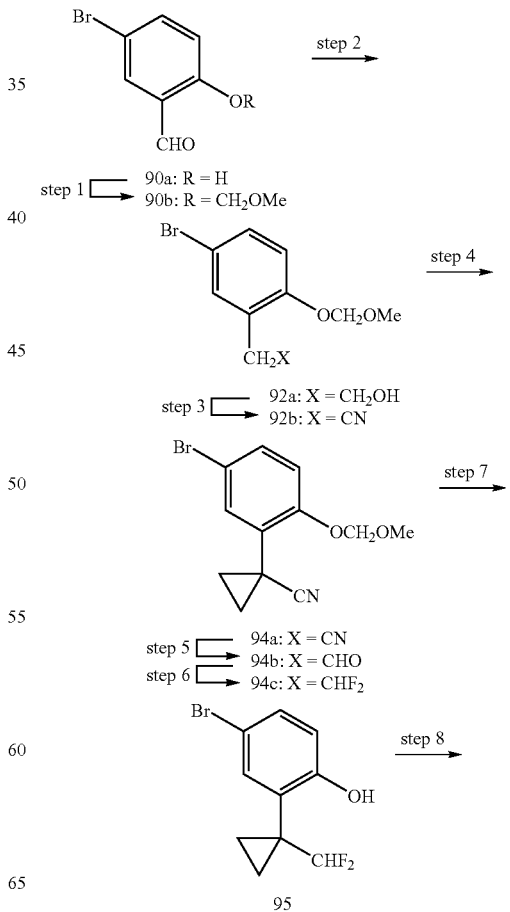

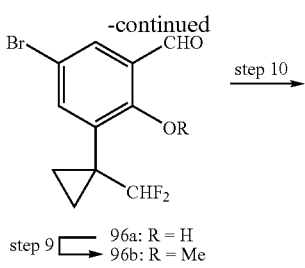

96a: R = H
96b: R = Me

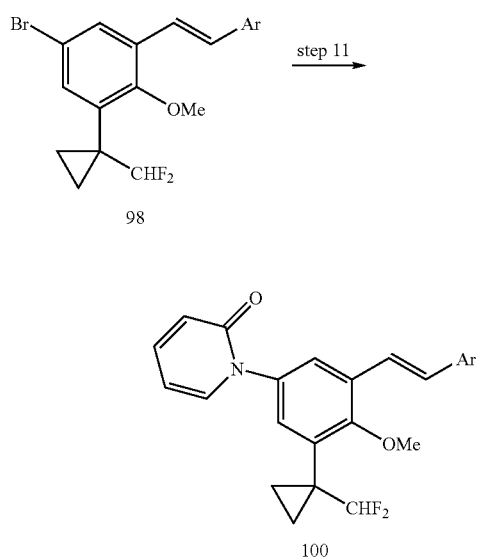

Ar = 4-methansulfonylamido-phenyl step 1—To a solution of 90a (10.0 g, 49.7 mmol) in DMF (100 mL) at RT was added $K_2CO_3$ (13.7 g, 99.4 mmol) followed by chloromethyl methyl ether (tech grade, 5.2 mL, 54.7 mmol). The reaction mixture was stirred at RT overnight then quenched with $H_2O$ and thrice extracted with EtOAc. The combined extracts were thrice washed with $H_2O$, dried ($MgSO_4$), filtered and concentrated to afford 11.6 g (96%) of 90b as a yellow oil.

step 2—To a solution of 90b (11.6 g, 47.3 mmol) in MeOH (100 mL) at 0° C. was slowly added $NaBH_4$ (1.87 g, 49.6 mmol). The reaction mixture was stirred at 0° C. for 1 h then quenched with $H_2O$ and brine. The resulting mixture was thrice extracted with EtOAc, dried ($MgSO_4$), filtered and concentrated to afford 11.3 g (97%) of alcohol 92a as a pale yellow oil.

step 3—To a solution of alcohol 92a (10.0 g, 40.5 mmol) in DCM (80 mL) at 0° C. were added TEA (7.3 mL, 52.6 mmol) and methanesulfonyl chloride (3.4 mL, 44.5 mmol). The reaction mixture was stirred for 1 h then quenched with $H_2O$ and extracted with DCM. The extracts were dried ($MgSO_4$), filtered and concentrated to a light yellow oil. To a solution of this oil in DMF (50 mL) was added LiBr (3.9 g, 44.5 mmol) and the reaction mixture was stirred at RT for 1 h. A solution of NaCN (3.0 g, 60.7 mmol) in $H_2O$ (5 mL) was slowly added, using an ice bath to control the exothermic reaction. After the addition was complete, the reaction mixture was stirred at RT for 1 h then quenched with $H_2O$ and thrice extracted with EtOAc (3×). The combined extracts were thrice washed with $H_2O$, dried ($MgSO_4$), filtered and concentrated to afford 10.5 g of nitrile 92b as a yellow oil.

step 4—To a solution of 92b (2.6 g, 10.1 mmol) in DMF (25 mL) at 0° C. was added NaH (60% in mineral oil, 0.89 g, 22.2 mmol). The reaction mixture was stirred at 0° C. for 0.5 h then 1,2-dibromoethane (0.96 mL, 11.1 mmol) was added dropwise. The reaction mixture was warmed to RT and stirred for 1 h then quenched with $H_2O$ and thrice extracted with EtOAc. The organic phase was thrice washed with $H_2O$ then dried ($MgSO_4$), filtered and concentrated. The residue was purified by $SiO_2$ chromatography eluting with 10% EtOAc/hexanes to afford 1.83 g (64%) of 94a as a yellow oil.

step 5—To a solution of 94a (1.83 g, 6.5 mmol) in DCM (40 mL) at −78° C. was added dropwise DIBAL (1.27 mL, 7.1 mmol). The reaction mixture was stirred at −78° C. for 2 h then quenched with MeOH (0.5 mL) and warmed to RT. A saturated solution of Rochelle's salt (40 mL) was added and the biphasic mixture was stirred vigorously for 30 min. The phases were separated and the aqueous phase was extracted with DCM. The combined extracts were dried ($MgSO_4$), filtered and concentrated. The crude residue was purified by $SiO_2$ chromatography eluting with 2% EtOAc/DCM to afford 1.49 g (81%) of 94b as a pale yellow oil.

step 6—To a solution of 94b (4.9 g, 17.2 mmol) in DCM (80 mL) was slowly added (diethylamino)sulfur trifluoride (6.8 mL, 51.6 mmol). The reaction mixture was stirred at RT overnight then quenched by slowly pouring the reaction mixture onto ice. The mixture was diluted with $H_2O$ and extracted with DCM. The combined extracts were dried ($MgSO_4$), filtered and concentrated. The crude residue was purified by $SiO_2$ chromatography eluting with 10% EtOAc/hexanes to afford 4.07 g (77%) of 94c as a colorless oil.

step 7—To a solution of 94c (4.05 g, 13.2 mmol) in DCM (60 mL) at 0° C. was added 4 Å powdered molecular sieves (4 g) followed by TMSBr (5.2 mL, 39.6 mmol). The reaction mixture was allowed to warm to RT and stirred overnight then filtered to remove the sieves which were rinsed with DCM. The filtrate was washed sequentially with sat'd. aq. $NaHCO_3$ and $H_2O$, dried ($MgSO_4$), filtered and concentrated. The crude residue was purified by $SiO_2$ chromatography eluting with an EtOAc/hexane gradient (10% to 20% EtOAc) to afford 2.85 g (82%) of 95 as a pale yellow oil.

step 8—To a solution of 95 (2.85 g, 10.8 mmol) in anhydrous MeCN (50 mL) was added TEA (5.6 mL, 40.5 mmol), $MgCl_2$ (1.54 g, 16.2 mmol), and paraformaldehyde (2.27 g, 75.6 mmol). The bright yellow reaction mixture was heated at reflux for 5 h then cooled to RT and quenched with 1.0 M aqueous HCl. The mixture was thrice extracted with EtOAc then the combined extracts were dried ($MgSO_4$), filtered and concentrated. The crude residue was purified by $SiO_2$ chromatography eluting an EtOAc/hexane gradient (10% to 20% EtOAc) to afford 1.04 g (33%) of 96a as an off-white solid.

step 9—To a solution of 96a (1.04 g, 3.6 mmol) in DMF (15 mL) was added $K_2CO_3$ (1.0 g, 7.2 mmol) followed by iodomethane (0.27 mL, 4.3 mmol). The reaction mixture was stirred at RT for 4 h then quenched with $H_2O$ and thrice extracted with EtOAc. The combined extracts were thrice washed with $H_2O$, dried ($MgSO_4$), filtered and concentrated to afford 1.06 g (97%) of 96b as a pale yellow solid which required no further purification.

The conversion of 96b to 98 steps can be carried out in accord with the procedures described in steps 2, 5 and 6 of example 1. The title compound is prepared by copper-catalyzed coupling of 98 and 1H-pyridin-2-one in accord with the procedure in example 8.

Example 15

N-(4-{(E)-2-[4-Methoxy-3,3-dimethyl-7-(2-oxo-2H-pyridin-1-yl)-2,3-dihydro-benzofuran-5-yl]-vinyl}-phenyl)-methanesulfonamide (114)

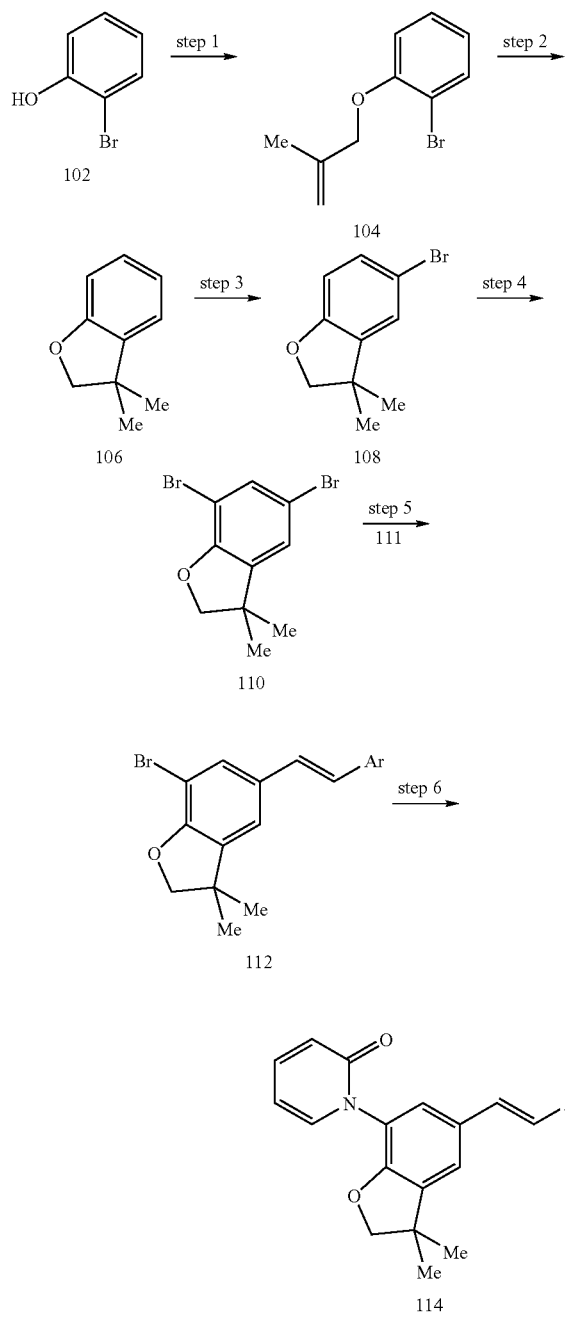

Ar = 4-methansulfonamido-phenyl step 1—To a solution of 102 (2.457 g, 14 mmol) and acetone (75 mL) was added K$_2$CO$_3$ (4.907 g, 36 mmol) and 3-bromo-1-methylpropene (2.0 mL, 20 mmol) and the resulting solution was heated at reflux overnight. The reaction mixture was cooled and concentrated in vacuo. The residue was partitioned between EtOAc (150 mL) and H$_2$O (40 mL) The aqueous phase was extracted with EtOAc and the combined organic extracts were sequentially washed with H$_2$O and brine, dried (Na$_2$SO4), filtered and concentrated in vacuo. The residue was purified by SiO$_2$ chromatography eluting with a EtOAc/hexane gradient (0 to 5% EtOAc) to afford 3.34 g (98.5%) of 104.

step 2—To a solution of 104 (3.33 g, 15 mmol) and benzene (150 mL) in a dried flask was added sequentially Bu$_3$SnH (6.625 g, 22 mmol) and AIBN (0.241 g) and the resulting solution heated at reflux overnight. The reaction mixture was cooled to RT, a 10% KF solution was added and the resulting two-phase mixture stirred vigorously for 2 h. The phases were separated and the organic phase was sequentially washed with sat'd NaHCO$_3$ (50 mL) and brine. The combined organic extracts were dried (Na$_2$SO$_4$), filtered and evaporated. The crude product was purified by SiO$_2$ chromatography eluting with a DCM/hexane gradient (0 to 10% DCM) to afford 1.855 g (85%) of 106.

step 3—To a solution of 106 (0.700 g, 5 mmol) and DMF (50 mL) in a dried flask was added NBS (1.765 g, 10 mmol) and the reaction was stirred overnight at RT. The reaction mixture was partitioned between H$_2$O (30 mL) and Et$_2$O (150 mL). The aqueous layer was separated and extracted with Et$_2$O (150 mL). The organic extracts were thrice washed with H$_2$O than once with brine. The combined organic extracts were dried (Na$_2$SO$_4$), filtered and concentrated in vacuo. The residue was adsorbed on SiO$_2$, added to the top of a SiO$_2$ column and eluted with hexanes to afford 0.9260 (90%) of 108.

step 4—To a solution of 108 (0.956 g, 4 mmol) and HOAc (8.0 mL) cooled to 0° C. was added a dropwise solution of Br$_2$ (320 µL, 6 mmol) and HOAc (2 mL) over a 10 min period. The reaction mixture was stirred overnight at RT. The reaction was quenched by addition of 10% Na$_2$S$_2$O$_3$ (10 mL) then HOAc was removed in vacuo. The residue was partitioned between Et$_2$O (100 mL) and sat'd. aq. NaHCO$_3$ (20 mL). The aqueous layer was separated and extracted with Et$_2$O (100 mL). The organic extracts were washed twice with sat'd. NaHCO$_3$ (20 mL) and once with H$_2$O. The combined extracts were dried (Na$_2$SO$_4$), filtered and evaporated. The residue was adsorbed on SiO$_2$, added to the top of a SiO$_2$ column and eluted with hexanes to afford 1.22 (95%) of 110.

step 5—Palladium-catalyzed coupling of 110 and 111 to afford 114 is carried out in accord with the procedure described in step 6 of example 13 except 88 was replaced with 111.

step 6—The title compound is prepared by copper-catalyzed coupling of 114 and 1H-pyridin-2-one in accord with the procedure in example 8.

N-{4-[(E)-2-(4,4,6-Trimethyl-[1,3,2]dioxaborinan-2-yl)-vinyl]-phenyl}-methanesulfonamide (111)—To a solution of Pd(OAc)$_2$ (0.076 g), tris-(ortho-tolyl)-phosphine (0.246 g, 1 mmol) and toluene (16 mL) were added sequentially N-(4-iodo-phenyl)-methanesulfonamide (2.00 g, 7 mmol, CASRN 102294-59-7), tributyl amine (1.92 mL) and 4,4,6-trimethyl-2-vinyl-[1,3,2]dioxaborinane (1.244 g, 8 mmol, CASRN 4627-10-5). The reaction was heated at reflux for 72 h, cooled to RT and partitioned between Et$_2$O (100 mL) and 1M HCl (20 mL). The aqueous layer was withdrawn and re-extracted with Et$_2$O. The organic phases were washed sequentially with H$_2$O and brine. The extracts were combined, dried (Na$_2$SO$_4$), filtered and evaporated. The residue was purified by SiO$_2$ chromatography eluting with an EtOAc/hexane gradient (0 to 30% EtOAc) to afford 1.4 g (58%) of 111.

Example 16

N-(4-{(E)-2-[3-(1-Chloro-cyclopropyl)-2-methoxy-5-(2-oxo-2H-pyrazin-1-yl)-phenyl]-vinyl}-phenyl)-methanesulfonamide (122)

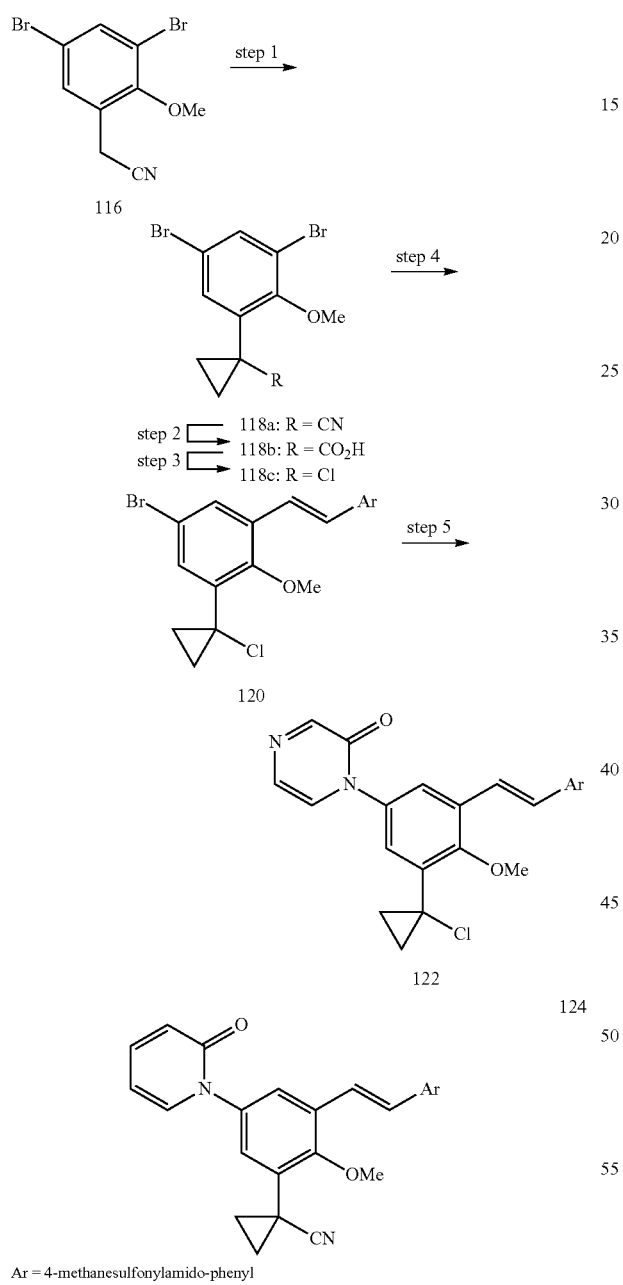

Ar = 4-methanesulfonylamido-phenyl step 1—To a solution of 2,4-dibromophenyl-acetonitrile (116, 16 mmol; CASRN 188347-48-0) in DMF (80 mL) is added sodium hydride (49 mmol, 60% in mineral oil) and the resulting mixture is stirred at RT until bubbling subsided. To the reaction mixture is slowly added 1,2-dibromoethane (3.5 g, 18 mmol) and stirring is continued for 1 h. $H_2O$ is added and the mixture extracted with $Et_2O$. The organic extract is washed consecutively with $H_2O$ and brine, dried ($Na_2SO_4$), filtered, and concentrated in vacuo. The crude product is purified by $SiO_2$ chromatography eluting with EtOAc/hexane to afford 118a.

step 2—To a slurry of 118a (4.6 g, 14 mmol) in EtOH (50 mL) is added an aq. solution of NaOH (25%, 22 mL, 140 mmol). The resulting mixture is stirred and heated at reflux for 16 h. The EtOH is removed under reduced pressure and concentrated aqueous HCl is added at 0° C. to make the solution acidic. The precipitate is recovered by filtration and washed with hexane to afford 118b.

step 3—To a slurry of 118b (6 mmol) in benzene (150 mL) is added LiCl (1.4 g, 34 mmol), and nitrogen gas is bubbled through the resulting mixture for 10 min. $Pb(OAc)_4$ (15 g, 34 mmol) is added, and nitrogen gas is again bubbled through the resulting mixture for 10 min, followed by heating at reflux for 4 d under nitrogen. After cooling to RT, the mixture is filtered and the solids are washed with EtOAc. Saturated aq. $NaHCO_3$ is added, the mixture is filtered again, and the layers are separated. The organic layer is washed with brine, dried ($Na_2SO_4$), filtered, and then concentrated in vacuo. The crude material is purified by $SiO_2$ chromatography eluting with EtOAc/hexane to afford 118c.

step 4—Palladium-catalyzed cross-coupling of 118c and 88 is carried out in accord with the procedure described in step 6 of example 13. The crude residue is purified by $SiO_2$ chromatography eluting with EtOAc/hexane.

step 5—The title compound I-122 is prepared by copper-catalyzed coupling of 98 and 1H-pyrazin-2-one in accord with the procedure in example 8.

N-(4-{(E)-2-[3-(1-Cyano-cyclopropyl)-5-(2-oxo-2H-pyridin-1-yl)-phenyl]-vinyl}-phenyl)-methanesulfonamide (124) can be prepared analogously utilizing 118a in place of 118c, omitting steps 2 and 3, and replacing 1H-pyrazin-2-one in step 5 with 1H-pyridin-2-one.

Example 17

N-{3-[3-tert-Butyl-2-methoxy-5-(2-oxo-1,2-dihydro-pyridin-3-yl)-phenyl]-1-oxo-isochroman-7-yl}-methanesulfonamide (I-9)

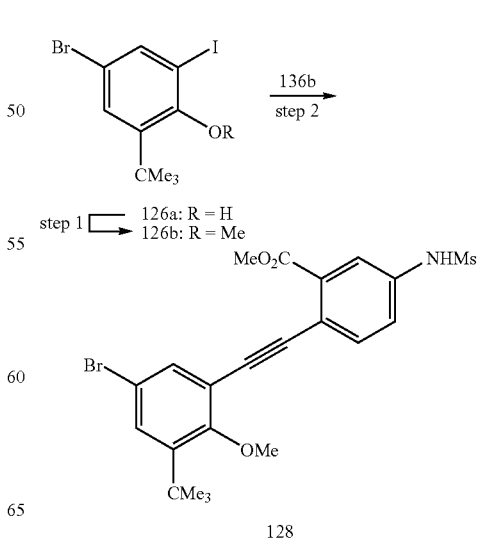

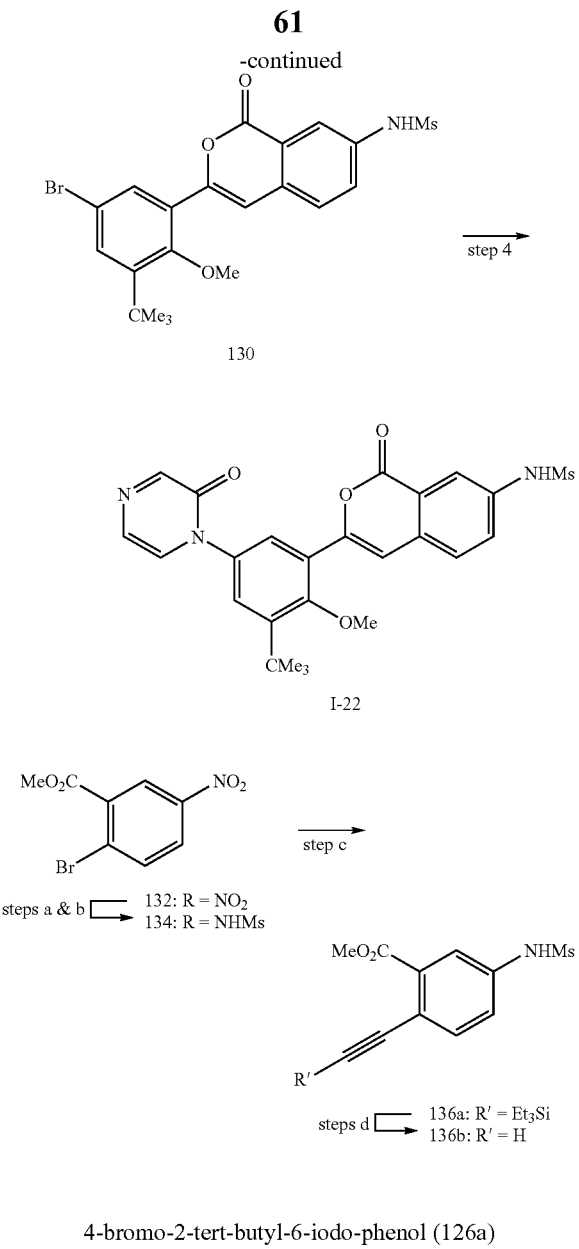

4-bromo-2-tert-butyl-6-iodo-phenol (126a)

To a ice-cold solution of 4-bromo-2-tert-butyl phenol (2.8 g, 86 wt %) dissolved in MeOH containing NaI (3.28 g) and NaOH (0.88 g) was added an aq. solution of NaOCl (4.5 wt %, 68.75 mL). The addition was continued until yellow color persisted (1.6 equivalents). To the resulting solution was added sat'd. aq. $Na_2SO_3$ (10 mL) and HOAc (2.5 mL) which resulted in the formation of a precipitate. The MeOH was evaporated and the residue suspended in $H_2O$ (50 mL) and aged at 40° C. for 2 h. then slowly cooled to RT. The solid was filtered, washed with $H_2O$ and dried in vacuo at 50° C. overnight to afford 6.74 g (87%) of 126a.

methyl 2-ethynyl-5-methanesulfonylamino-benzoate (136b)

step a—To a mixture of 132 (1.5 g, 5.8 mmol, CASRN 100959-29-6) and $NH_4Cl$ (3.1 g, 58 mmol) in MeOH (50 mL) and $H_2O$ (25 mL) heated to 70° C. was added iron powder (1.62 g, 29 mmol) over a period of 60 min. After addition was completed, stirring was continued for 45 min, and then cooled. The reaction mixture was filtered through CELITE and washed with MeOH. The filtrate was concentrated and partitioned between $H_2O$ and EtOAc. The organic phase was washed with brine, dried ($MgSO_4$), filtered and concentrated to afford 1.34 g (100%) of methyl 2-bromo-5-amino-benzoate (133).

step b—To a solution of 133 (1.34 g, 5.8 mmol) in DCM (30 mL) cooled to 5° C. was added TEA (4.04 ml, 2.52 g, 29 mmol), followed by dropwise addition of a solution of methanesulfonyl chloride (1.08 mL, 1.6 g, 14 mmol) in DCM (10 mL) over a period of 15 min. The reaction mixture was stirred at RT overnight, quenched with aqueous 1N HCl, and extracted with EtOAc. The combined extracts were washed with brine, dried ($MgSO_4$), filtered and concentrated to afford 4.5 g (100%) of 134.

step c—To a solution of the (triethylsilyl)acetylene (630 mg, 4.5 mmol) in DMF (25 mL) was added CuI (57 mg, 0.3 mmol) and $PPh_3$ (420 mg, 0.06 mmol). This solution mixture was purged with argon for 5 min then $PdCl_2(PPh_3)_2$ (15.4 mg, 0.02 mmol) was added followed by 134 (1.16 g, 3.0 mmol) and TEA (12 mL). Argon was bubbled through the solution and the reaction mixture was heated at 75° C. for 6 h under an argon atmosphere. The mixture was cooled, quenched with aqueous 1N HCl and twice extracted with EtOAc. The organic solution was washed sequentially with $H_2O$ and brine, dried ($MgSO_4$), filtered and concentrated. The crude material was purified by $SiO_2$ chromatography eluting with an EtOAc/hexane gradient (10% to 45% EtOAc) to afford 1.66 g (70%) of 136a.

step d—To a solution of 136a (1.66 g, 4.5 mmol) in THF (75 mL) cooled −30° C. was added dropwise, over a period of 15 min, a solution of tetrabutylammonium fluoride (5 mL, 1M solution in THF). The reaction mixture was stirred RT overnight and poured into aq. sat'd. $NH_4Cl$ solution. The resulting solution was extracted with EtOAc and the extracts washed with brine, dried ($MgSO_4$), filtered and concentrated. The crude material was purified by $SiO_2$ chromatography eluting with an EtOAc/hexane gradient (10% to 60% EtOAc) to afford 0.889 g (78%) of 136b.

step 1—To a solution of 126a (4.40 g, 12.4 mmol), iodomethane (7.7 mL, 17.6 g, 124 mmol) in acetone (80 mL) was added the $K_2CO_3$ (8.60 g, 62 mmol) and the resulting solution was stoppered and stirred overnight at RT. The reaction mixture was diluted with hexanes (100 mL) and the mixture was filtered over a plug of $SiO_2$. The filtrated was concentrated to afford 4.6 g (100%) of 126b.

step 2—A solution 136b (230 mg, 0.91 mmol), 126b (400 mg, 0.11 mmol), CuI (17 mg, 0.091 mmol), $PdCl_2(PPh_3)_2$ (130 mg, 0.18 mmol), TEA (5 mL) in DMF (10 mL) was stirred at 70° C. for 2 h. The mixture was cooled, quenched with aq. 1N HCl and twice extracted with EtOAc. The combined extracts were washed sequentially with $H_2O$ and brine, dried ($MgSO_4$), filtered and concentrated. The crude material was purified by $SiO_2$ chromatography eluting with an EtOAc/hexane gradient (10% to 70% EtOAc) to afford 191 mg (42%) of 128.

step 3—A tube was charged with 128 (978 mg, 19.8 mmol), $AuCl_3$ (30 mg) and TFA (4 mL), sealed and irradiated in a microwave reactor at 100° C. for 45 min. The mixture was cooled and concentrated. The crude product was purified by $SiO_2$ chromatography eluting with an EtOAc/hexane gradient (10% to 60% EtOAc) to afford 0.95 g (100%) of 130.

step 4—Cu-catalyzed amination of 130 to afford I-22 was carried our in accord with the procedure in example 8 except 62 was replaced with 1H-pyrazin-2-one.

Example 18

N-{2-[3-tert-Butyl-2-methoxy-5-(2-oxo-tetrahydro-pyrimidin-1-yl)-phenyl]-benzooxazol-5-yl}-methanesulfonamide (I-24)

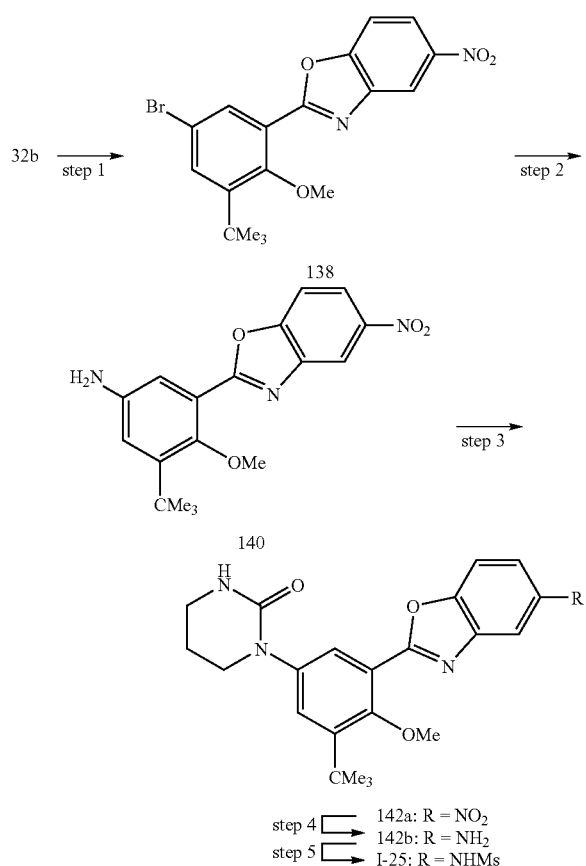

step 1—A tube was charged with solution of 2-amino-4-nitro-phenol (1.2 g, 7.7 mmol, CASRN 99-57-0) and EtOH and a solution of 32b (2.1 g, 7.7 mmol) and EtOH, sealed and heated at 90° C. overnight. The reaction mixture was cooled to RT and concentrated in vacuo. The resulting brown oil was taken up in DCM and treated with dichloro-dicyano-quinone (1.9 g, 8.4 mmol). The solution was stirred at RT for 1 h, then diluted with DCM (60 mL) and twice washed with sat'd. aq. NaHCO₃ and once with brine, dried (MgSO₄), filtered and concentrated in vacuo. The crude product was purified by SiO₂ chromatography eluting with an EtOAc/hexane gradient (0 to 5% EtOAc) to afford 1.0 g (31%) of 138.

step 2—A flask was charged with 138 (1.00 g, 2.4 mmol), benzophenone imine (0.7 g, 3.9 mmol, Pd₂(dba)₃ (90 mg, 0.10 mmol), BINAP (0.74 g, 0.10 mmol), NaO-tert-Bu (0.32 g, 3.3 mmol) and flushed with vacuum-Ar cycles. Toluene (40 mL) was added and the resulting solution heated at 80° C. overnight. The reaction mixture was cooled and filtered taken-up in EtOAc, washed with brine, dried (MgSO₄), filtered and concentrated. The residue was dissolved in MeOH (70 mL) and 50% aq. NH₂OH (10 mL) was added and the reaction mixture was stirred overnight at room temperature. The crude product was purified by SiO₂ chromatography eluting with an EtOAc/hexane gradient (5 to 20% EtOAc) to afford 400 mg of 140.

step 3—To a solution of 140 (0.400 g, 1.1 mmol) and THF was added 3-chloropropyl-isocyanate (120 μL, 1.1 mmol, CASRN 13010-19-0) and the solution stirred for 4.5 h at RT. The solution was diluted with EtOH (12 mL) and treated with aq. 1M KOH (12 mL). The resulting solution was heated at reflux overnight. The solution was cooled to RT and thrice extracted Et₂O and the combined extracts dried (MgSO₄), filtered and concentrated in vacuo. The crude product was purified to SiO₂ chromatography eluting with a gradient of EtOAc/hexanes (20% to 50% EtOAc) to 60:10:1 DCM:MeOH:NH₄OH (100%) to afford 0.100 g (23%) of 142a.

steps 4 & 5—Reduction of the nitro group and sulfonylation of the resulting amine were carried out in accord with the procedures described in steps 5 and 6 of Example 1 to afford I-25. The product was purified by SiO₂ chromatography eluting with a gradient of DCM/60:10:1 DCM:MeOH:NH₄OH (80% to 50% to 0% DCM).

Example 19

N-(4-{(E)-2-[3-tert-Butyl-5-(1,1-dioxo-1λ⁶-[1,2,6]thiadiazinan-2-yl)-2-methoxy-phenyl]-vinyl}-phenyl)-methanesulfonamide (I-26)

To a solution of 52a (0.144 g, 0.385 mmol) in DCM (8 mL) and TEA (1.0 mL) cooled to 5° C. was added N-(3-chloropropyl)sulfamoyl chloride (0.085 g, 0.44 mmol, CASRN 42065-72-5) and the resulting solution stirred at RT overnight. The solution was diluted with EtOAc, washed sequentially with 1N HCl and brine, dried and concentrated in vacuo. The residue was dissolved in DMSO (3 mL) and K₂CO₃ (0.16 g, 1.0 mmol) was added at RT then heated to 70° C. until the reaction was complete. The solution was cooled and partitioned between EtOAc and 1N HCl. The aqueous phase was separated and re-extracted with EtOAc. The combined organic extracts were washed with brine, dried, filtered and concentrated in vacuo. The crude product was split unto 4 aliquots and each purified on a preparative SiO₂ TLC plate developed with 60% EtOAc/hexane and the recovered solid combined, triturated with Et₂O and dried to afford 10.8 mg of I-26.

I-20 was prepared analogously except N-(3-chloropropyl) sulfamoyl chloride was replaced with N-(2-chloroethyl)sulfamoyl chloride (CASRN 53627-11-5).

Example 20

N-(4-{(E)-2-[3-tert-Butyl-2-methoxy-5-(3-methyl-5-oxo-1,5-dihydro-[1,2,4]triazol-4-yl)-phenyl]-vinyl}-phenyl)-methanesulfonamide (I-27)

To a solution of 58 (374 mg) in MeCN (9.5 mL) and MeOH (0.5 mL) was added MeC(OEt)₃ (0.20 mL, 1.1 equiv.), methyl hydrazinecarboxylate (0.100 g) and p-TsOH.H₂O (5 mg) and the resulting solution was heated at reflux overnight. The solution was cooled to RT and NaOMe was added (2.0 mL, 0.5M NaOMe in MeOH) was added and the solution heated at reflux overnight. The solution was acidified with HOAc and partitioned between H₂O and EtOAc. The aqueous layer was extracted with EtOAc and the combine EtOAc fractions were dried and concentrated in vacuo. The crude product was purified by SiO2 chromatography eluting with a NeOH/DCM gradient (0 to 10% MeOH and the recovered product further purified by dividing into four fractions each of which was purified on a preparative SiO2 preparative plate developed with 5% MeOH/DCM. The recovered product from the plates afford 145 mg of I-27.

Example 22

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µL enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from $7.5 \times 10^{-5}$ M to $20.6 \times 10^{-6}$ M), 1 µM each ATP, CTP, and GTP, 40 mM Tris-HCl pH 8.0, 40 mM NaCl, 4 mM DTT (dithiothreitol), 4 mM MgCl2, and 5 µL of compound serial diluted in DMSO. Reaction mixtures were assembled in 96-well filter plates (cat #MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µL of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft®) and Activity-Base® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control.

The compound concentration at which the enzyme-catalyzed rate of RNA synthesis was reduced by 50% ($IC_{50}$) was calculated by fitting equation (i) to the data where "Y"

$$Y = \% \text{ Min} + \frac{(\% \text{ Max} - \% \text{ Min})}{\left[1 + \frac{X}{(IC_{50})^S}\right]} \quad (i)$$

corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

Example 22

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and *luciferase* activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µl of 1×*R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the *luciferase* activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE II

| Compound Number | HCV Replicon Activity $IC_{50}$ (μM) | Cytotoxic Activity $CC_{50}$ (μM) |
| --- | --- | --- |
| I-13 | 0.0186 | 21.4 |
| I-5 | 0.019 | 13.8 |

Example 23

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |

-continued

Composition for Oral Administration (C)

| Ingredient | % wt./wt. |
| --- | --- |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:
1. A compound according to formula I wherein:

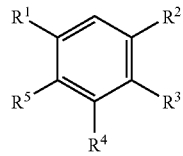

$R^1$ is 2-oxo-2H-pyrazin-1-yl-said 2-oxo-2H-pyrazin-1-yl moiety optionally independently substituted with one or two halogen or $C_{1-3}$ alkyl substitutents;

$R^2$ is (a) —$CR^{2a}$=$CR^{2a}Ar$, (b) —$(C(R^{2b})_2)_n Ar$, (c) 1-oxo-1H-isochromen-7-yl or 2H-isoquinolin-1-one either optionally substituted by $NR^a R^b$, or, (d) benzooxazol-2-yl or benzothiazol-2-yl either optionally substituted by $NR^a R^b$;

$R^{2a}$ is independently in each occurrence hydrogen, $C_{1-3}$ alkyl, cyano, carboxyl or halogen;

$R^{2b}$ is independently in each occurrence hydrogen or $C_{1-3}$ alkyl, cyano, carboxyl, $C_{1-3}$ hydroxyalkyl or $C_{1-3}$ alkoxy-$C_{1-3}$ alkyl;

$R^3$ is hydrogen, $C_{1-6}$ alkoxy, $C_{1-6}$ alkyl, $C_{1-6}$ haloalkyl, $C_{1-6}$ haloalkoxy or halogen or $R^3$ and $R^{4a}$ together are $CH_2$—O or $(CH_2)_2$ and together with atoms to which they are attached form a 2,3-dihydrobenzofuran or an indane;

Ar is (a) aryl or (b) heteroaryl wherein said heteroaryl is pyridin-2-yl, pyridin-3-yl pyrazin-2-yl or pyridizin-3-yl and said aryl or said heteroaryl are optionally independently substituted with one to three substitutents selected from the group consisting of hydroxy, $C_{1-6}$ alkoxy, $C_{1-6}$ alkyl, $C_{1-6}$ hydroxyalkyl, $C_{1-3}$ alkoxy-$C_{1-6}$ alkyl, halogen, $(CH_2)_n NR^a R^b$, cyano, $C_{1-6}$ alkoxycarbonyl, carbamoyl, N-alkylcarbamoyl, N,N-dialkylcarbamoyl, $(CH_2)_n CO_2 H$, $SO_2 NH_2$, $C_{1-6}$ alkylsulfinyl and $C_{1-6}$ alkylsulfonyl;

$R^a$ and $R^b$ are independently hydrogen, $C_{1-6}$ alkyl, $C_{1-6}$ haloalkyl, $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, —$SO_2$—$NR^c R^d$, $C_{1-3}$ alkylcarbamoyl or $C_{1-3}$ dialkylcarbamoyl;

$R^c$ and $R^d$ are (i) independently hydrogen, $C_{1-3}$ alkyl or $(CH_2)_{2-6} NR^e R^f$ or (ii) together with the nitrogen to which they are attached are $(CH_2)_2 X^5 (CH_2)_2$ wherein $X^5$ is O or $NR^i$ and $R^i$ is hydrogen, $C_{1-3}$ alkyl, $C_{1-3}$ acyl or $C_{1-3}$ alkylsulfonyl;

$R^e$ and $R^f$ are independently in each occurrence hydrogen or $C_{1-3}$ alkyl;

$R^4$ is hydrogen, $C_{1-6}$ alkyl, $C_{1-6}$ haloalkyl, $C_{3-5}$ cycloalkyl, halogen, $C_{1-6}$ alkoxy, $C_{1-3}$ haloalkoxy or $CR^{4a}R^{4b}R^{4c}$ wherein:
(i) $R^{4a}$, $R^{4b}$ and $R^{4c}$ are independently selected from $C_{1-3}$ alkyl, $C_{1-2}$ alkoxy, $C_{1-2}$ fluoroalkyl, $C_{1-3}$ hydroxyalkyl, cyano or hydroxy; or,
(ii) when taken together, $R^{4a}$ and $R^{4b}$ together are $C_{2-4}$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl, or $R^{4a}$ and $R^{4b}$ together with the carbon to which they are attached are 3-oxetanyl, or tetrahydrofuran-2-yl; or,
(iii) either $R^5$ or $R^3$ and $R^{4a}$ together are $CH_2$—O or $(CH_2)_2$ and together with atoms to which they are attached form a 2,3-dihydro-benzofuran or an indane and $R^{4b}$ and $R^{4c}$ are $C_{1-3}$ alkyl;

$R^5$ is hydrogen or halogen or $R^5$ and $R^{4a}$ together are $CH_2$—O or $(CH_2)_2$ and together with atoms to which they are attached form a 2,3-dihydrobenzofuran or an indane;

n is independently in each occurrence zero to three; or,
a pharmaceutically acceptable salt thereof.

2. A compound according to claim 1 wherein $R^2$ is —$CR^{2a}$=$CR^{2a}Ar$ or —$(C(R^{2b})_2)_n Ar$.

3. A compound according to claim 2 wherein Ar is phenyl substituted at least by $(CH_2)_n NR^a R^b$ at the 4-position wherein n is zero.

4. A compound according to claim 3 wherein:
$R^2$ is —$CR^{2a}$=$CR^{2a}Ar$,
$R^{2a}$ is hydrogen,
$R^a$ is $C_{1-6}$ alkylsulfonyl,
$R^b$ is hydrogen,
$R^3$ is hydrogen or $C_{1-6}$ alkoxy,
$R^4$ is trifluoromethyl or $CR^{4a}R^{4b}R^{4c}$ wherein $R^a$, $R^b$ and $R^c$ are methyl.

5. A compound according to claim 1 wherein $R^2$ is —$CR^{2a}$=$CR^{2a}Ar$ and $R^4$ is $CR^{4a}R^{4b}R^{4c}$ wherein $R^{4a}$ together with one of $R^5$ or $R^3$ are $CH_2$—O or $(CH_2)_2$ and $R^{4a}$ and $R^5$ or $R^3$ together with atoms to which they are attached form a 2,3-dihydro-benzofuran or an indane and $R^{4b}$ and $R^{4c}$ are $C_{1-3}$ alkyl and the other of $R^5$ or $R^3$ is hydrogen in the case of $R^5$ or hydrogen or $C_{1-6}$ alkoxy in the case of $R^3$.

6. A compound according to claim 1 wherein $R^2$ is —$CR^{2a}$=$CR^{2a}Ar$ and $R^4$ is $CR^{4a}R^{4b}R^{4c}$ and $R^{4a}$ and $R^{4b}$ together are $C_2$ alkylene and $R^{4c}$ is hydrogen, $C_{1-3}$ alkyl, $C_{1-2}$ alkoxy, halogen, $C_{1-3}$ hydroxyalkyl, cyano or $C_{1-2}$ fluoroalkyl or $R^{4a}$ and $R^{4b}$ together with the carbon to which they are attached are 3-oxetanyl, or tetrahydrofuran-2-yl and $R^{4c}$ is methyl.

7. A compound according to claim 1 wherein $R^2$ is —$CR^{2a}$=$CR^{2a}Ar$ and $R^4$ is trifluoromethyl.

8. A compound according to claim 1 selected from the group consisting of:
N-(4-{(E)-2-[3-tert-butyl-2-methoxy-5-(2-oxo-2H-pyrazin-1-yl)-phenyl]-vinyl}-phenyl)-methanesulfonamide;
N-{3-[3-tert-butyl-2-methoxy-5-(2-oxo-2H-pyrazin-1-yl)-phenyl]-1-oxo-1H-isochromen-7-yl}-methane-sulfonamide;
N-(4-{(E)-2-[3-tert-butyl-2-methoxy-5-(2-oxo-2H-pyrazin-1-yl)-phenyl]-vinyl}-3-methoxymethyl-phenyl)-methanesulfonamide;
2-{(E)-2-[3-tert-butyl-2-methoxy-5-(2-oxo-2H-pyrazin-1-yl)-phenyl]-vinyl}-5-methanesulfonylamino-benzoic acid methyl ester;
2-{(E)-2-[3-tert-butyl-2-methoxy-5-(2-oxo-2H-pyrazin-1-yl)-phenyl]-vinyl}-5-methanesulfonylamino-benzoic acid;
N-(4-{(E)-2-[3-tert-butyl-2-methoxy-5-(2-oxo-2H-pyrazin-1-yl)-phenyl]-vinyl}-3-hydroxymethyl-phenyl)-methanesulfonamide;
2-{(E)-2-[3-tert-butyl-2-methoxy-5-(2-oxo-2H-pyrazin-1-yl)-phenyl]-vinyl}-benzoic acid; or,
a pharmaceutically acceptable salt thereof.

9. A method for treating a Hepatitis C Virus (HCV) infection comprising administering to a patient in need thereof, a therapeutically effective quantity of a compound according to claim 1.

10. The method of claim 9 further co-comprising administering at least one immune system modulator and/or at least one antiviral agent that inhibits replication of HCV.

11. The method of claim 10 wherein the immune system modulator is an interferon, interleukin, tumor necrosis factor or colony stimulating factor.

12. The method of claim 11 wherein the immune system modulator is an interferon or chemically derivatized interferon.

13. The method of claim 10 wherein the antiviral compound is selected from the group consisting of a HCV protease inhibitor, another HCV polymerase inhibitor, a HCV helicase inhibitor, a HCV primase inhibitor and a HCV fusion inhibitor.

14. A method for inhibiting replication of HCV in a cell by contacting the cell with a compound according to claim 1.

15. A pharmaceutical composition comprising a compound according to claim 1 admixed with at least one pharmaceutically acceptable carrier, diluent or excipient.

* * * * *